US007250267B2

(12) United States Patent
Walt et al.

(10) Patent No.: US 7,250,267 B2
(45) Date of Patent: Jul. 31, 2007

(54) CROSS-REACTIVE SENSORS

(75) Inventors: David R. Walt, Lexington, MA (US); Caroline L. Schauer, Silver Spring, MD (US); Frank J. Steemers, San Diego, CA (US)

(73) Assignee: Trustees of Tufts College, Medford, MA (US)

( * ) Notice: Subject to any disclaimer, the term of this patent is extended or adjusted under 35 U.S.C. 154(b) by 55 days.

(21) Appl. No.: 10/221,815

(22) PCT Filed: Mar. 14, 2001

(86) PCT No.: PCT/US01/08126

§ 371 (c)(1), (2), (4) Date: Mar. 5, 2003

(87) PCT Pub. No.: WO01/69245

PCT Pub. Date: Sep. 20, 2001

(65) Prior Publication Data

US 2007/0122861 A1   May 31, 2007

(51) Int. Cl.
*C12Q 1/48* (2006.01)
*C12Q 1/34* (2006.01)
*C12Q 1/44* (2006.01)
*C12Q 1/37* (2006.01)
*C12Q 1/00* (2006.01)

(52) U.S. Cl. ............................. 435/15; 435/4; 435/18; 435/19; 435/23

(58) Field of Classification Search ............... 435/7.9, 435/18, 19, 23, 24, 25; 436/172, 164, 165
See application file for complete search history.

(56) References Cited

U.S. PATENT DOCUMENTS

| 3,999,122 | A | * | 12/1976 | Winstel et al. ............ 324/71.1 |
| 4,832,369 | A | * | 5/1989 | Johnson et al. ............. 281/18 |
| 5,320,814 | A | | 6/1994 | Walt et al. ............... 422/82.07 |
| 5,512,490 | A | * | 4/1996 | Walt et al. .................. 436/171 |
| 5,690,894 | A | | 11/1997 | Pinkel et al. .............. 422/68.1 |
| 6,004,494 | A | * | 12/1999 | Debe ........................... 264/104 |
| 6,306,285 | B1 | * | 10/2001 | Narayanan et al. ......... 205/787 |
| 6,331,438 | B1 | * | 12/2001 | Aylott et al. ................. 436/172 |
| 6,350,369 | B1 | * | 2/2002 | Lewis et al. ............. 205/777.5 |
| 6,680,206 | B1 | * | 1/2004 | McDevitt et al. ........... 436/172 |

FOREIGN PATENT DOCUMENTS

| DE | 194 40 098 A | 4/1997 |
| WO | WO 00/04372 | 7/1999 |

OTHER PUBLICATIONS

Dickinson et al. Anal. Chem. 1999, vol. 71, pp. 2192-2198.*
Steemers et al. Book of Abstracts, 216th ACS National Meeting. 1998. Abstract 050.*
Alfonta et al., "Sensing of acetycholine by tricomponent-enzyme layered electrode using fardaic impedance spectroscopy, cyclic voltammetry, and microgravimetric quartz crystal microbalance transduction methods", *Anal. Chem.*, 2000, 72: 927-935.
Dickinson et al., "A chemical-detecting system based on a cross-reactive optical sensor array", *Nature*, 1996, 382: 697-700.
Dickinson et al., "Convergent self-encoded bead sensor arrays in the design of an artificial nose", Anal. Chem., 1999, 71: 2191-2198.
Janes et al., "Quantitative screening of hydrolyase libraries using pH indicators: identifying active and enantioselective hydrolases", *Chem. Eur. J.*, 1998, 4: 2324-2331.
Johnson et al., "Identification of mulitple analytes using an optical sensor array and pattern recognition neural networks", *Anal. Chem.*, 1997, 69: 4641-4648.
Nanjee et al., "Sequential microenzymatic assay of cholesterol, triglycerides, and phospholipids in a single aliquot", *Clinical Chem.*, 1996, 42: 915-926.
Schauer et al., "Cross-reactive optical sensor arrays", *Abstracts of Papers American Chemical Society*, 2000, 219: 1-2, 219th National Meeting of the American Chemcial Society, San Francisco, CA.
Schaeuer et al., "A cross-reactive, class-selective enzymatic array assay", *J. Am. Chem. Soc.*, 2001, 123: 9443-9444.
Steemer et al., "Cross-reactive enzyme biosensor for analysis of alcohol mixtures", *Abstracts of Papers American Chemical Society*, 1998, 216: 1-3, 216th National Meeting of the American Chemical Society, Boston, MA.
White et al., "Rapid analyte recognition in a device based on optical sensors and the olfactory system", *Anal. Chem.*, 1996, 68, 2191-2202.

* cited by examiner

*Primary Examiner*—Christopher R. Tate
(74) *Attorney, Agent, or Firm*—Chaote, Hall & Stewart LLP; Brenda H. Jarrell

(57) ABSTRACT

The present invention provides a novel cross-reactive sensor system utilizing cross-reactive recognition elements. In the inventive system, each of said one or more cross-reactive recognition elements is capable of interacting with more than one species of liquid analyte of interest, whereby each of said one or more cross-reactive recognition elements reacts in a different manner with each of said one or more species of liquid analytes of interest to produce a detectable agent of each analyte of interest, whereby said detectable agent is analyzed and the information is processed for data acquisition and interpretation. In certain preferred embodiments, the detectable agent and/or change is detected directly, while in certain other preferred embodiments, the detectable agent and/or change is detected with the help of a transducing agent capable of relaying information about each detectable agent generated for each of said species of liquid analyte of interest, whereby said information is processed for data acquisition and interpretation. The present invention also provides method for the analysis of analytes comprising contacting one or more analytes with the inventive system described above.

49 Claims, 31 Drawing Sheets

Initial results of Esterases
5 substrates are distinguishable by two esterases using PCA.
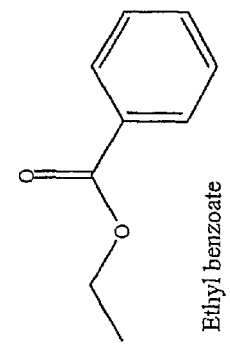
Ethyl benzoate
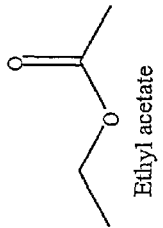
Ethyl acetate
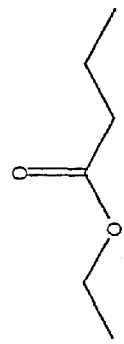
Butyric acid ethyl ester
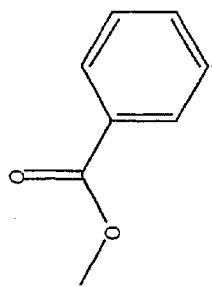
Methyl Benzoate
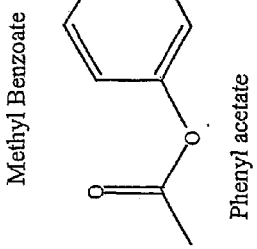
Phenyl acetate
Figure 2

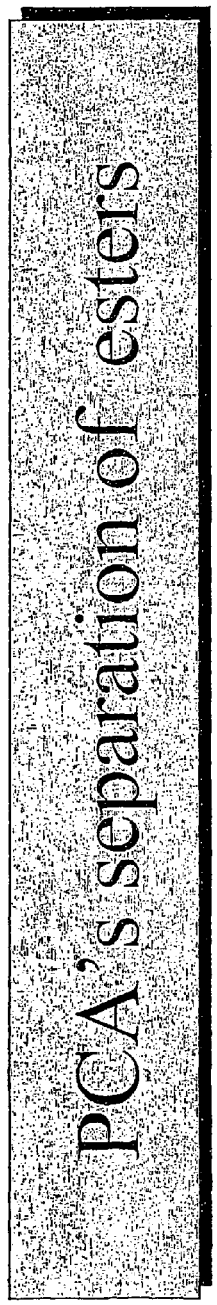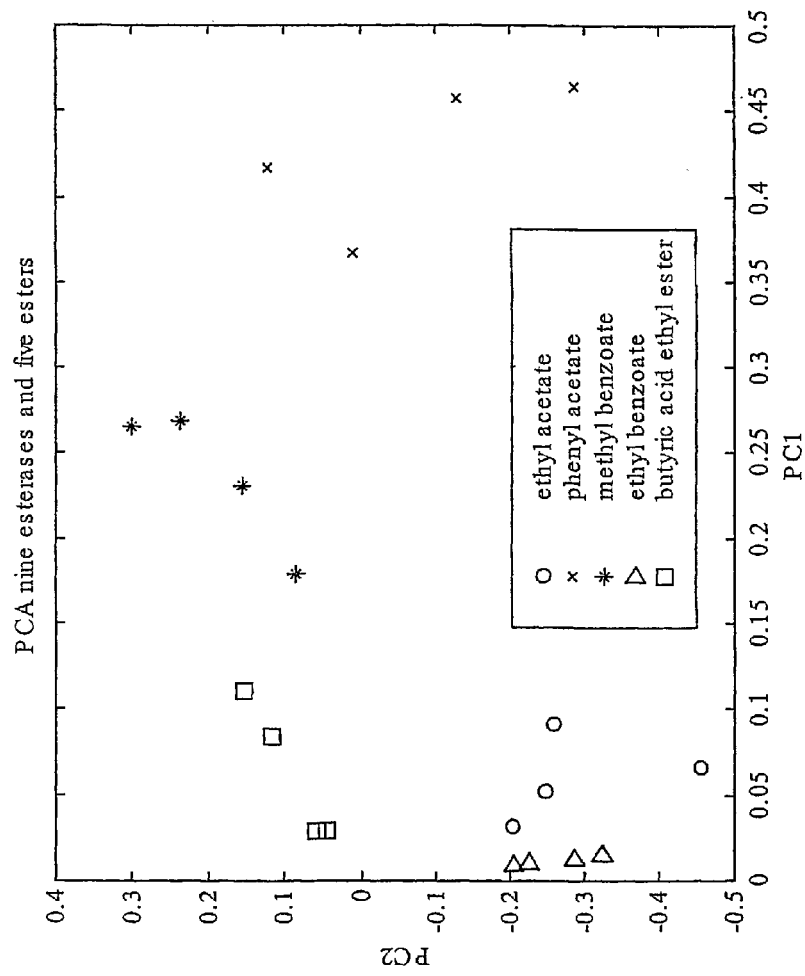
Figure 3

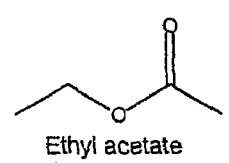
Ethyl acetate
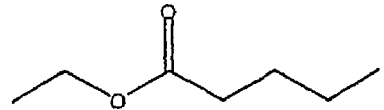
Ethyl benzoate
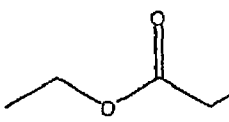
Ethyl Propionate
Ethyl valerate
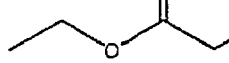
Butyric acid ethyl ester
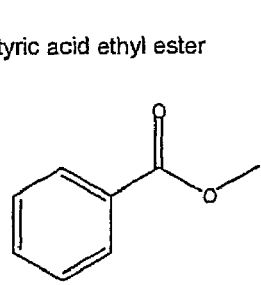
methyl nicotinate
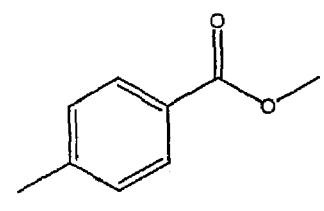
methyl methyl nicotinate
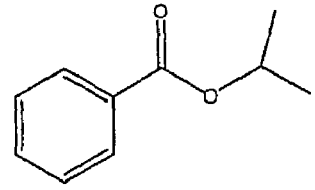
Isopropyl nicotinate
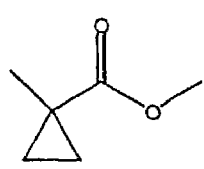
methyl methyl glycidate
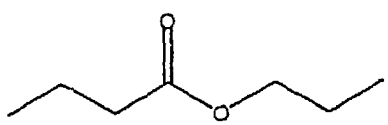
Propyl butyrate
Figure 4

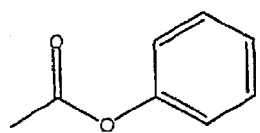
Phenyl acetate
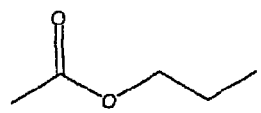
Propyl acetate
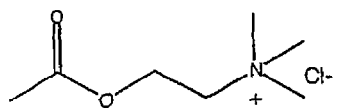
Acetylcholine
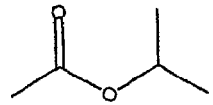
Isopropyl acetate
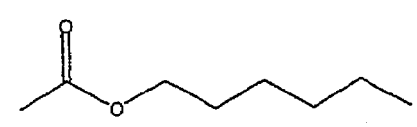
Hexyl acetate
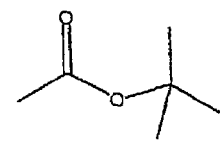
t-butyl acetate
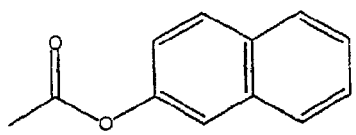
2-napthyl acetate
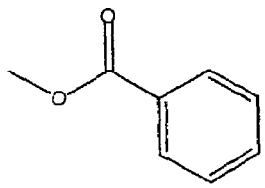
Methyl Benzoate
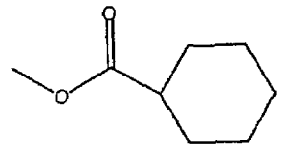
Methyl cyclohexane carboxylate
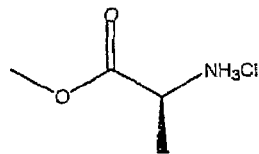
L-alanine methyl ester
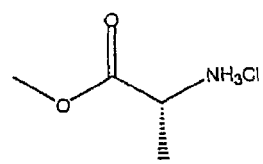
D-alanine methyl ester
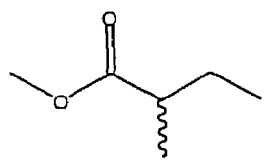
Methyl methyl butyrate
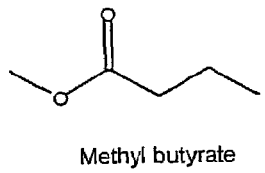
Methyl butyrate
Figure 5

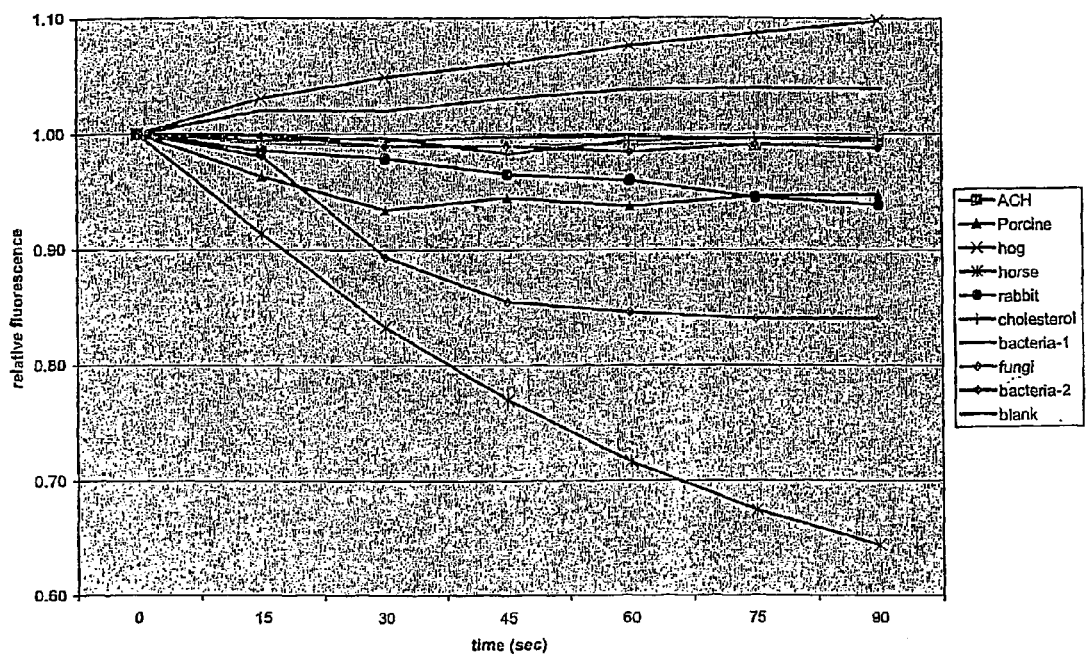
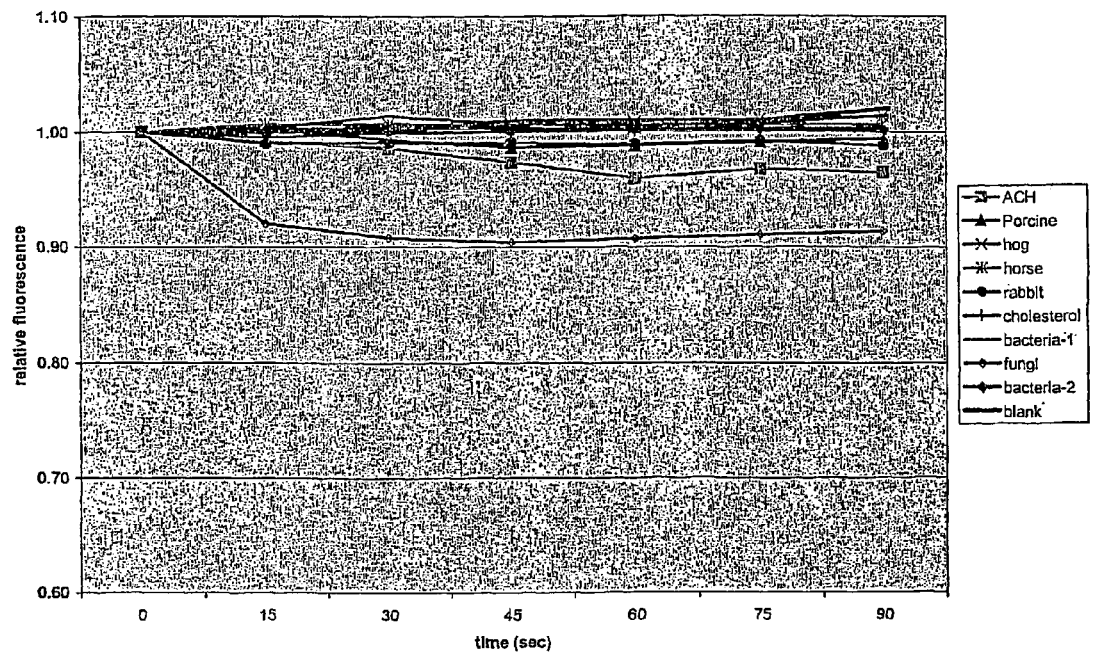
Figure 6

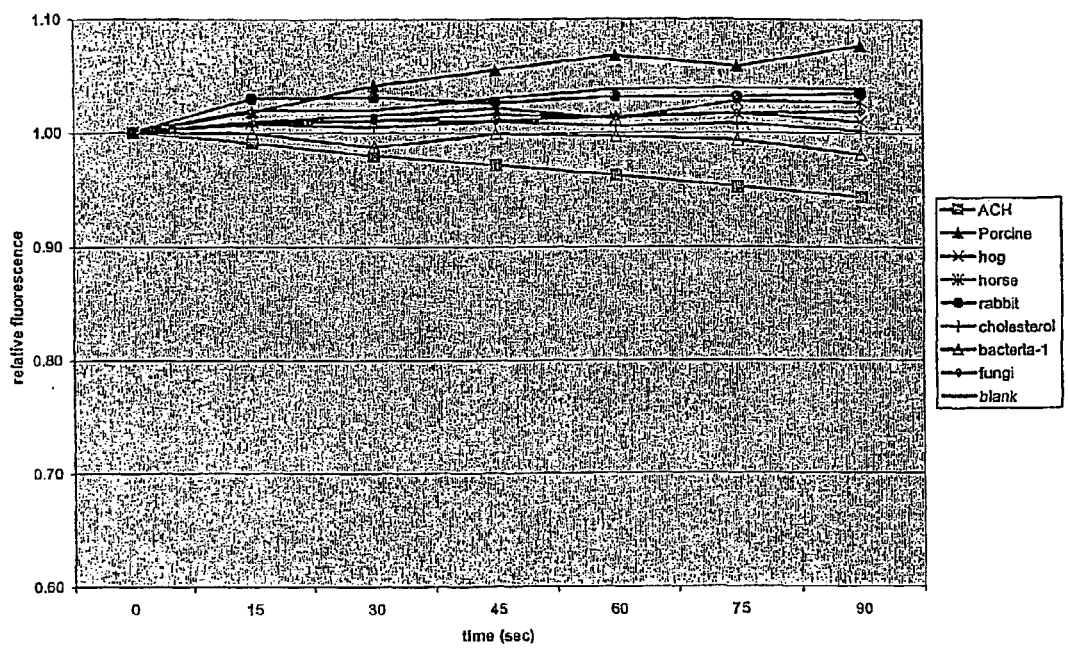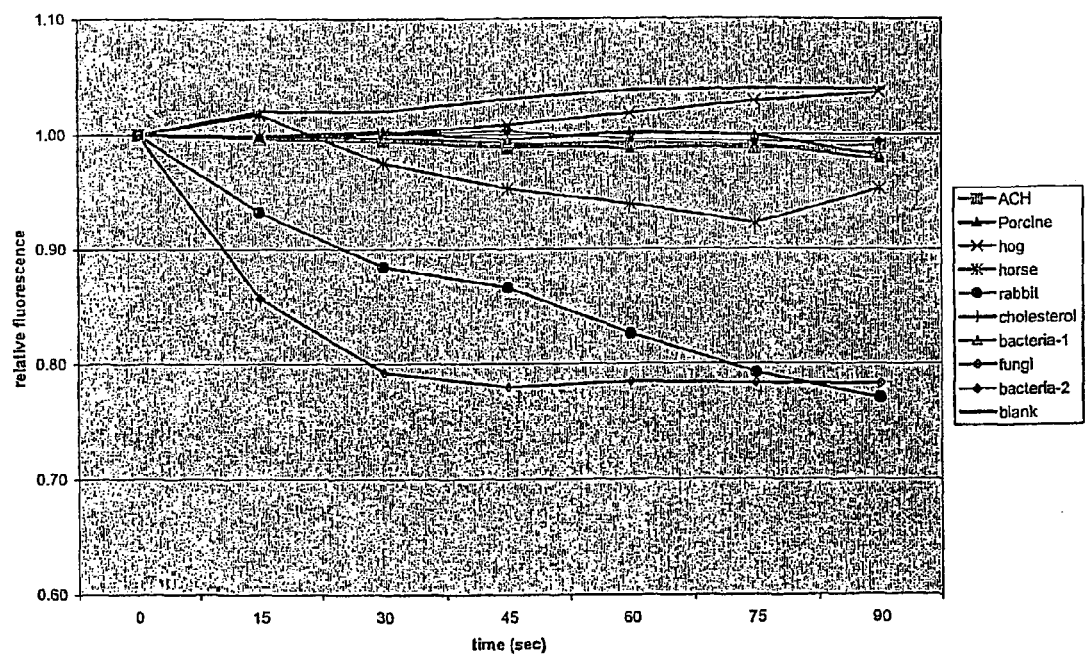
Figure 13

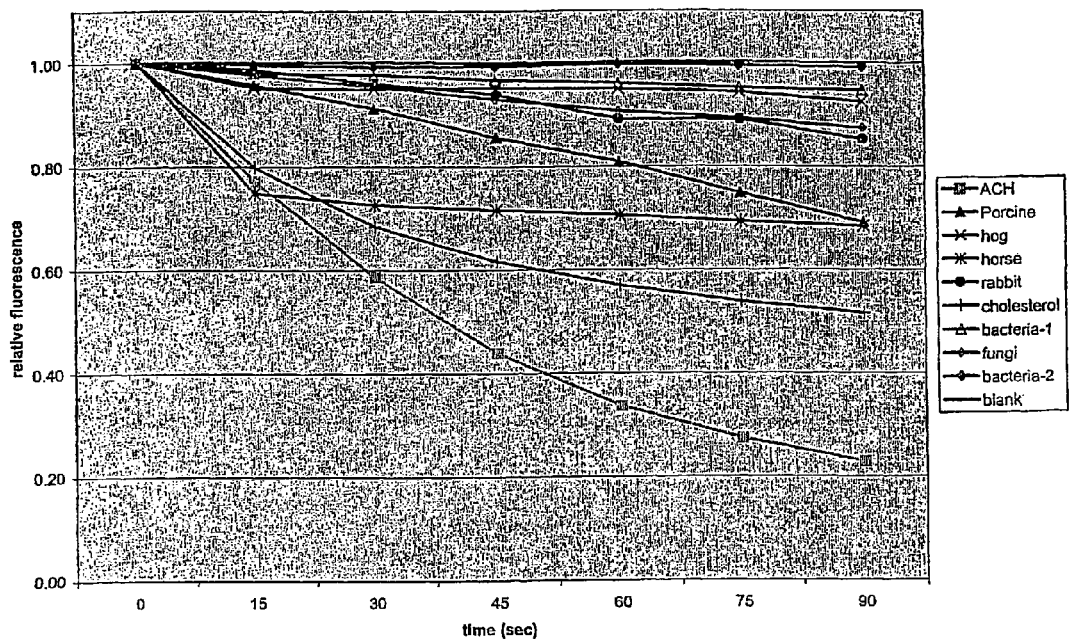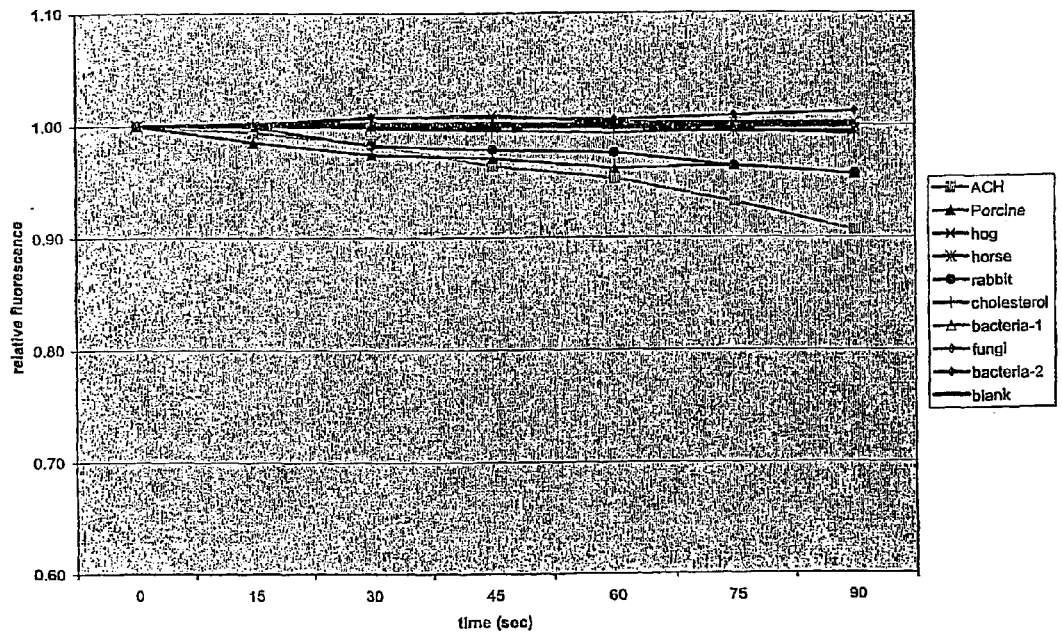
Figure 15

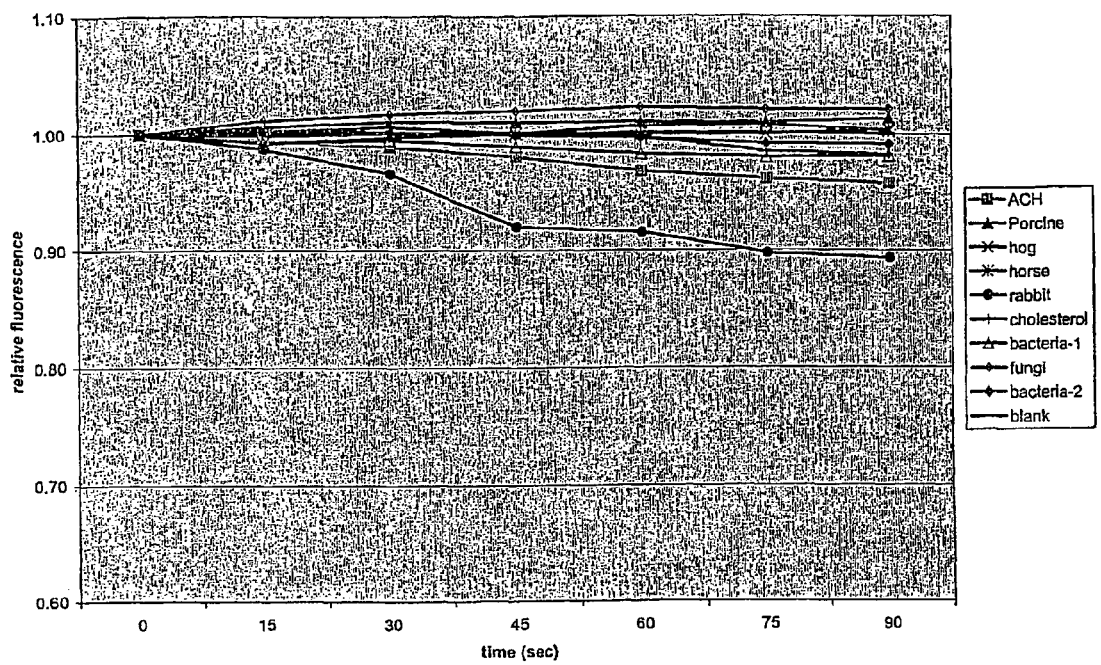
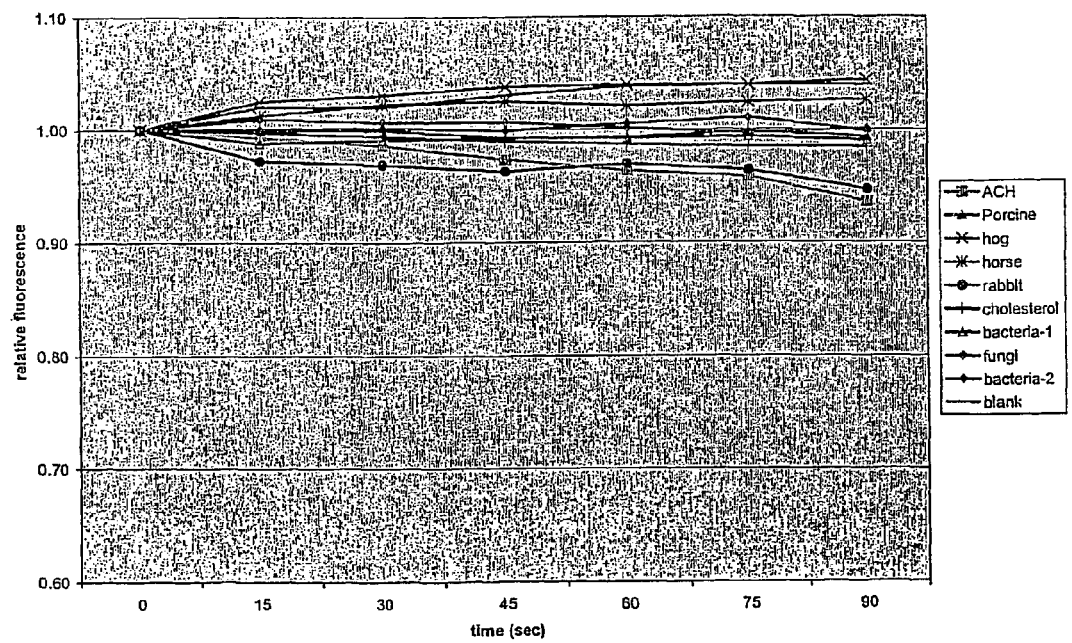
Figure 16

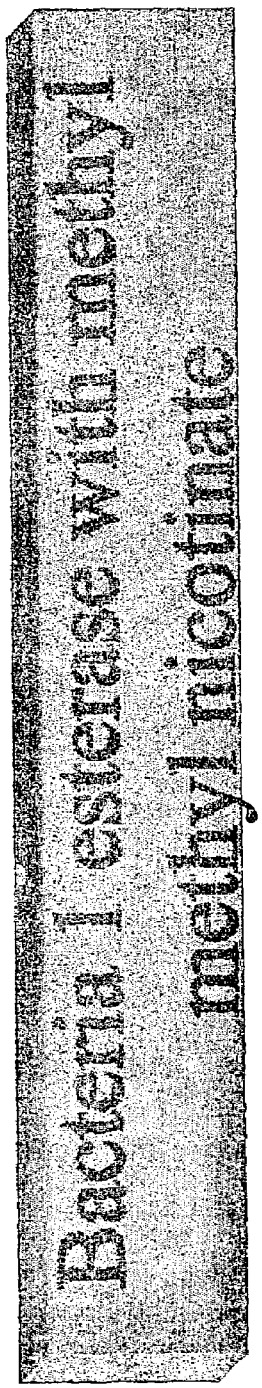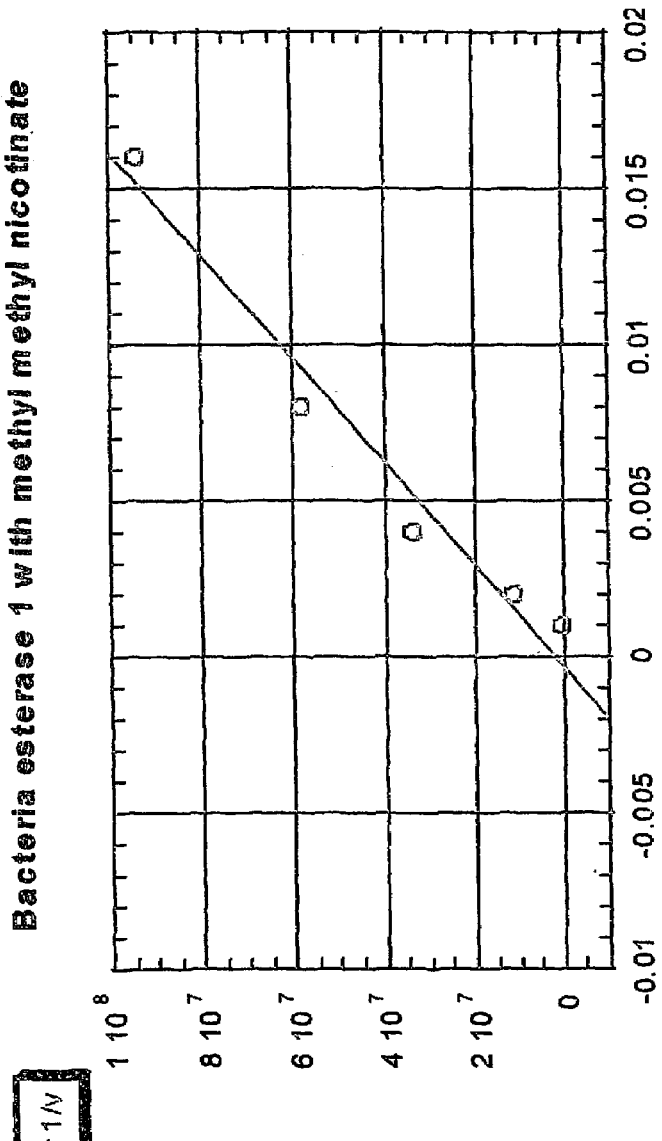
Figure 20

| MNI | fungi | choles | porcine | horse | hog | rabbit | ACH | bac1 | blank |
|---|---|---|---|---|---|---|---|---|---|
| Day 1 | -5.8E+05 | -2.6E+04 | -5.7E+05 | -2.2E+04 | -4.2E+05 | -1.5E+05 | -8.2E+04 | -1.7E+04 | 1.3E+04 |
| Day 2 | -7.8E+05 | -3.8E+04 | -6.5E+05 | -3.8E+04 | -4.0E+05 | -1.6E+05 | -7.5E+04 | -2.0E+04 | 2.6E+04 |
| Day 3 | -8.2E+05 | -4.4E+04 | -5.6E+05 | -1.1E+04 | -5.3E+05 | -2.6E+05 | -6.3E+04 | -1.4E+04 | 4.9E+04 |
| Day 4 | -7.1E+05 | -5.2E+04 | -6.1E+05 | -1.7E+04 | -4.8E+05 | -1.8E+05 | -4.7E+04 | -5.7E+03 | 3.4E+04 |
| Day 5 | -8.4E+05 | -5.2E+04 | -7.2E+05 | -1.2E+04 | -3.5E+05 | -1.7E+05 | -5.2E+04 | -1.3E+04 | 4.1E+04 |
| Day 6 | -6.5E+05 | -4.7E+04 | -6.3E+05 | -6.2E+03 | -4.0E+05 | -1.7E+05 | -2.6E+04 | -2.7E+04 | 6.5E+04 |
| Day 7 | -6.5E+05 | -1.3E+05 | -5.3E+05 | -1.4E+04 | -2.8E+05 | -1.2E+05 | -4.4E+04 | -2.3E+04 | 2.9E+04 | slope of the reaction in fluorescence units/time (sec)

Figure 22

|  | EA | PA | MB | EB | BA | PRA | MC | EP | HA | TB | MMBU | MBU | IA | PB | EV | AC | NA | DM | LM | MNI | MMNI | IN | MMG |
|---|---|---|---|---|---|---|---|---|---|---|---|---|---|---|---|---|---|---|---|---|---|---|---|
| EA | 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| PA | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 |
| MB | 0 | 0 | 4 | 0 | 0 | 0 | 0 | 0 | 0 | 0 | 0 | 0 | 0 | 0 | 0 | 0 | 0 | 0 | 0 | 0 | 0 | 0 | 0 |
| EB | 0 | 0 | 0 | 4 | 0 | 0 | 0 | 0 | 0 | 0 | 0 | 0 | 0 | 0 | 0 | 0 | 0 | 0 | 0 | 0 | 0 | 0 | 0 |
| BA | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 |
| PRA | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 |
| MC | 0 | 0 | 0 | 0 | 0 | 0 | 4 | 0 | 0 | 0 | 0 | 0 | 0 | 0 | 0 | 0 | 0 | 0 | 0 | 0 | 0 | 0 | 0 |
| EP | 0 | 0 | 0 | 0 | 0 | 0 | 0 | 4 | 0 | 0 | 0 | 0 | 0 | 0 | 0 | 0 | 0 | 0 | 0 | 0 | 0 | 0 | 0 |
| HA | 0 | 0 | 0 | 0 | 0 | 0 | 0 | 0 | 4 | 0 | 0 | 0 | 0 | 0 | 0 | 0 | 0 | 0 | 0 | 0 | 0 | 0 | 0 |
| TB | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 |
| MMBU | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 0 |
| MBU | 0 | 0 | 0 | 0 | 1 | 0 | 0 | 0 | 0 | 1 | 0 | 4 | 0 | 0 | 0 | 0 | 0 | 0 | 0 | 0 | 0 | 0 | 0 |
| IA | 0 | 0 | 0 | 0 | 0 | 0 | 0 | 0 | 0 | 0 | 0 | 0 | 4 | 0 | 0 | 0 | 1 | 0 | 0 | 0 | 0 | 0 | 0 |
| PB | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 |
| EV | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 |
| AC | 0 | 0 | 0 | 0 | 0 | 0 | 0 | 0 | 0 | 1 | 0 | 0 | 0 | 0 | 0 | 4 | 0 | 0 | 0 | 0 | 0 | 0 | 0 |
| NA | 0 | 0 | 0 | 0 | 0 | 2 | 0 | 0 | 0 | 0 | 0 | 0 | 0 | 0 | 0 | 0 | 3 | 0 | 0 | 0 | 0 | 0 | 0 |
| DM | 0 | 0 | 0 | 0 | 0 | 0 | 0 | 0 | 0 | 0 | 0 | 0 | 0 | 0 | 0 | 0 | 0 | 4 | 0 | 0 | 0 | 0 | 0 |
| LM | 0 | 0 | 0 | 0 | 0 | 0 | 0 | 0 | 0 | 0 | 0 | 0 | 0 | 0 | 0 | 0 | 0 | 0 | 4 | 0 | 0 | 0 | 0 |
| MNI | 0 | 0 | 0 | 0 | 0 | 0 | 0 | 0 | 0 | 0 | 0 | 0 | 0 | 0 | 0 | 0 | 0 | 0 | 0 | 4 | 0 | 0 | 0 |
| MMNI | 0 | 0 | 0 | 0 | 0 | 0 | 0 | 0 | 0 | 0 | 0 | 0 | 0 | 0 | 0 | 0 | 0 | 0 | 0 | 0 | 4 | 0 | 0 |
| IN | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 0 |
| MMG | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 |

Figure 24

Actual vs. Calculated

Figure 30

Highlighted Regions of Confusion Matrix for Proteases actual

| Albumin | Human | Pig | Horse | Sheep |
|---------|-------|-----|-------|-------|
| Human   |       | 0   | 0     |       |
| Pig     | 0     |     | 0     | 0     |
| Horse   | 0     | 0   |       | 0     |
| Sheep   |       | 0   | 0     |       | calculated

70% of the incorrect assignments were due to the albumins.

Figure 31

CROSS-REACTIVE SENSORS

GOVERNMENT SUPPORT

The work described herein was supported by Office of Naval Research contract N00014-95-1-1340 and National Institutes of Health grant GM 48142. Therefore, the government may have certain rights in this invention.

BACKGROUND OF THE INVENTION

The ability to more efficiently detect and analyze specific components (analytes) of a mixture or sample would greatly benefit medicine, environmental analysis, and consumer industries (e.g., food analysis), to name a few. For example, the food industry depends upon chemical analysis for quality control, environmentalists depend upon chemical analysis for the detection of harmful agents in natural resources, such as water, and the medical community depends upon analysis for the detection of agents such as metabolites, drugs, and glucose to name a few. Although many methods suitable for sensing applications have been developed (see, for example, Wolfbeis et al., *Analytica Chim. Acta,* 1991, 250, 181), there still remains a need to develop chemical sensors that are capable of detecting analytes with specificity and selectivity.

In general, a sensor device includes the following: 1) a recognition element capable of identifying and interacting with the analyte which usually is contained in low concentration in a mixture of a variety of other components; 2) a transducer element that can transform the recognition process into a measurable signal; and 3) a processing unit, which, after amplification of the primary signal, converts it into a familiar readout (e.g., pH, ppm, etc.). One approach that has been utilized in the development of more selective sensors is the use of bioorganic species (enzymes, ion carriers, and natural or synthetic receptor/carriers) that are believed to mimic the selectivity of nature and undergo specific reactions with the entity to be recognized, resulting in specific recognition and, consequently, sensing. The difficulty with this approach, however, is that identification of agents that can selectively interact with analytes of interest can be problematic. For example, synthetic receptors often exhibit poor selectivity, and have difficulties in transducing the recognition process. Additionally, these approaches have generally focused on the interaction of one specific agent with one analyte, creating a cumbersome system if many analytes need to be detected. It would thus be desirable to develop a system that would minimize the number of recognition elements necessary, whereby the recognition elements utilized would be cross-reactive, thus each interacting with more than one analyte to generate a unique agent and/or change that can be readily detected.

Towards this end, Walt et al. (see, for example, Dickinson et al., *Anal. Chem.* 1999, 71, 2192; White et al., *Anal. Chem.* 1996, 68, 2191; Dickinson et al., *Nature* 1996, 382, 697) described a novel approach, the "artificial nose", in which high-density optical arrays that directly incorporate a number of structural and operational features of the olfactory system were developed for the cross-reactive analysis of vapors. Clearly, it would also be desirable if an efficient and sensitive cross-reactive sensor system could be developed for the analysis of liquid analytes, preferably in an array format for high-throughput complex analysis.

SUMMARY OF THE INVENTION

In recognition of the need for the development of novel and efficient sensors, the present invention provides a sensor system for liquid analytes comprising one or more cross-reactive recognition elements, wherein each of said one or more cross-reactive recognition element is capable of interacting with more than one species of liquid analyte of interest, whereby each of said one or more cross-reactive recognition elements reacts in a different manner with each of said one or more species of liquid analytes of interest to produce a detectable agent for each analyte of interest, and whereby said detectable agent is analyzed and the information is processed for data acquisition and interpretation. In other preferred embodiments the sensor system employs at least two or more cross-reactive recognition elements, for example, two to five cross reactive recognition elements or two to ten cross-reactive recognition elements. In yet other preferred embodiments, the sensor system employs at least ten or more cross reactive recognition elements. In a final embodiment, the present invention employs at least fifty or more cross-reactive recognition elements. For example, the "artificial nose" currently utilizes 39 equivalents of the cross-reactive recognition elements described herein.

In certain embodiments, the detectable agent and/or change can be analyzed directly, however in certain other embodiments, a transducer agent is present, whereby said transducer is capable of relaying information about each detectable agent generated for each of said species of liquid analyte of interest, whereby said information is processed for data acquisition and interpretation. Thus, in another aspect, the present invention provides a system for analysis comprising 1) a sensor system as described above, wherein the sensor system optionally includes a transducer; and 2) a processing unit, which, after amplification of the primary signal, converts it into a familiar signal for subsequent data analysis.

In yet another aspect, the present invention provides a method for the analysis of analytes that involves contacting one or more analytes of interest with a cross-reactive sensor system as described above, and analyzing the agents and/or change associated with the interaction. It will be appreciated that this agent and/or change is either analyzed directly, or with the help of a transducer. In certain embodiments, a processing unit (e.g., fluorescence detector) is utilized for the analysis of the agent and/or change associated with the interaction of the cross-reactive recognition element and the analytes of interest. It will also be appreciated that the method of the present invention may further include a chemoinformatic step, for example a step involving computational analysis, to sort, analyze, or process the data obtained.

In certain embodiments of the inventive sensor system, the system for analysis, and the method of analysis, as described above, the cross-reactive recognition elements are provided in array format having a plurality of addresses, whereby each address in the array contains one cross-reactive recognition element. In certain other preferred embodiments, one or more cross-reactive recognition elements are provided in array format having a plurality of addresses, whereby each address in the array contains more than one cross-reactive element. In still other embodiments, two or more of the addresses contains the same type of cross-reactive recognition element.

Alternatively, the inventive sensor system for analysis and the method of analysis attaches the cross-reactive recognition elements to a solid support, for example, beads or resin.

The cross-reactive recognition element on the solid support are contacted with the analyte(s) of interest for capture and/or reaction with, and identification of, the analyte of interest. Alternatively, the solid support containing the cross-reactive recognition element, e.g., a bead, is placed in array format having a plurality of addresses, whereby each address in the array contains one bead having an attached cross-reactive recognition element. In certain other preferred embodiments, one or more beads having attached cross-reactive recognition elements are provided in array format having a plurality of addresses, whereby each address in the array contains more than one bead having an attached cross-reactive element. Finally, as with the array described above, two or more of the addresses may further contain beads having the same type of cross-reactive recognition element.

In certain embodiments of the present invention, each of said one or more cross-reactive recognition elements is an enzyme or a receptor. Exemplary enzymes for use in the present invention include, but are not limited to those selected from the group consisting of esterases, hydrolases, isomerases, lysases, transferases, oxido-reductases, and ligases. In certain embodiments, the enzyme is an esterase selected from the group consisting of esterase from rabbit liver, esterase from porcine liver, acetylcholine esterase from electrophorous electricus, cholesterol esterase from hog pancrease, esterase from hog liver, esterase from horse liver, esterase from *mucor miehei*, esterase from *bacillus* sp., and esterase from *bacillus thermoglucosidasius*.

Exemplary receptors include receptors wherein the binding event is coupled to the transduction scheme, e.g., antibody, protein, and small molecule receptors. In certain embodiments of the present invention, the cross-reactive recognition element is a receptor selected from the group consisting of chemosensors, phosphorescent chemosensors, cryptands, carcerands, hemicarcerands, hemicarceplexes, carceplexes, spherands, hemispherands, cryptahemispherands, coraplexes, velcraplexes, cyclophanes, cyclic oligonucleotides, cyclic ureas, cyclic peptides, nanotubes, discrete aggregates, clefts and polyaza clefts, macrolactams, macrobicyclics, macrocyclics, macrotricyclics, calix[n]arenes, crown ethers, cyclodextrins, hemispherands, cages, chlorophyls, cavitands, cavitand dimers, catenanes, grids, polymers, double and triple helicates, porphryns, viruses, self-assembling enzymes, DNA, RNA, peptides, proteins, micelles, fibers and discs.

As mentioned above, in certain embodiments of the present invention, a transducer is also present, wherein said transducer is selected from the group consisting of electrochemical transducer, optical transducer, thermal transducer, and acoustic transducer. Exemplary electrochemical transducers include, but are not limited to those having an energy transduction mode selected the group consisting of amperometric, conductimetric, impedimetric, potentiometric, and potentiometric stripping analysis. Exemplary optical transducers include, but are not limited to, those having an energy transduction mode selected from the group consisting of absorbance, chemiluminescence, electrogenerated chemiluminescence, fluorescence, fluorescence lifetime, fiber optic waveguides, near-field microscopy, near-field spectroscopy, near-infrared, planar waveguides, surface enhanced raman, and surface plasmon resonance. In certain preferred embodiments, the optical transducer is a pH sensitive dye, including, but not limited to, those selected from the group consisting of fluorescein, carboxyfluorescein, SNAFL, SNARF, LysoSensor Green DND-189, Oregon Green, NERF, LysoSensor Yellow/Blue DND-160, HPTS (pyranine), BCECF, BCPCF, and Bodipy. In other preferred embodiments, the optical transducer comprises an oxygen sensitive dye, including, but not limited to Ru(4,7-diphenyl-1,10-phen)$_3$(Cl)$_2$, Ru(bipy)$_3$Cl$_2$ and trans-1(2'-methoxyvinyl)pyrene. Exemplary acoustic transducers include, but are not limited to those having an energy transduction mode selected from the group consisting of acoustic plate mode, flexural plate mode, surface acoustic wave, surface transverse wave, and thickness shear mode. Exemplary thermal transducers include, but are not limited to those having an energy transduction mode selected from the group consisting of adiabatic and heat transduction.

DESCRIPTION OF THE DRAWING

The invention is described with reference to the several figures of the drawing, in which.

FIG. 2 depicts five initially tested esters that are distinguishable by two esterases.

FIG. 3 depicts the separation of five esters using nine esterases.

FIG. 4 depicts certain exemplary analytes (esters).

FIG. 5 depicts certain exemplary analytes (esters).

FIG. 6 depicts the relative fluorescence versus time for methylcyclohexane carboxylate and for methyl 2-methyl butyrate.

FIG. 13 depicts the relative fluorescence versus time for D-alanine methyl ester and for ethyl propionate.

FIG. 15 depicts the relative fluorescence versus time for phenyl acetate and for methyl benzoate.

FIG. 16 depicts the relative fluorescence versus time for ethyl benzoate and for butyric acid ethyl ester (ethyl butyrate).

FIG. 20 depicts a Lineweaver-Burk plot of various concentrations of methyl 6-methyl nicotinate with bacteria esterase 1. Vmax and Km values are $4 \times 10^{-7}$ Ms$^{-1}$ and 2.6 mM, respectively.

FIG. 21 depicts a Lineweaver-Burk plot of various concentrations of ethyl valerate with bacteria esterase 1. Vmax and Km values are $2 \times 10^{-7}$ Ms$^{-1}$ and 1 mM, respectively.

FIG. 22 is a table that depicts the slope of the reaction of nine different esterases with methyl 6-methyl nicotinate in fluorescence units/time from data collected over a number of days.

FIG. 24 depicts a principal component analysis (PCA) confusion matrix that indicates the actual vs. the calculated identity of twenty-three ester analytes based on reaction rates with nine different esterases. Esterases are Rabbit Liver, Porcine liver, Horse liver, Hog liver, *Mucor miehei* (fungi), *Bacillus* sp. (bacteria-1), *Bacillus* th. (bacteria-2), Acetylcholine Esterase from Electrophorus electricus, and Cholesterol Esterase from hog pancreas. Esters are ethyl propionate (EP), ethyl benzoate (EB), ethyl valerate (EV), ethyl acetate (EA), ethyl butyrate (BA), propyl butyrate (PB), isopropyl nicotinate (IN), isopropyl acetate (IA), methyl 2-methyl butyrate (MMBU), methyl butyrate (MBU), methyl benzoate (MB), methyl 2-methyl glycidate (MMG), methyl nicotinate (MNI), methyl 6-methyl nicotinate (MMNI), methyl cyclohexane carboxylate (MC), L-alanine methyl ester (LM), D-alanine methyl ester (DM), t-butyl acetate (TB), hexyl acetate (HA), 2-naphthyl acetate (NA), acetylcholine chloride (AC), phenyl acetate (PA), and propyl acetate (PRA).

FIG. 30 depicts a PCA confusion matrix for protein analytes digested with the seven cross-reactive proteases.

FIG. 31 depicts highlighted regions of the principal component analysis (PCA) confusion matrix of FIG. 30 for albumin protein analytes digested with the seven cross-reactive proteases.

DETAILED DESCRIPTION OF THE INVENTION

Figure 1:
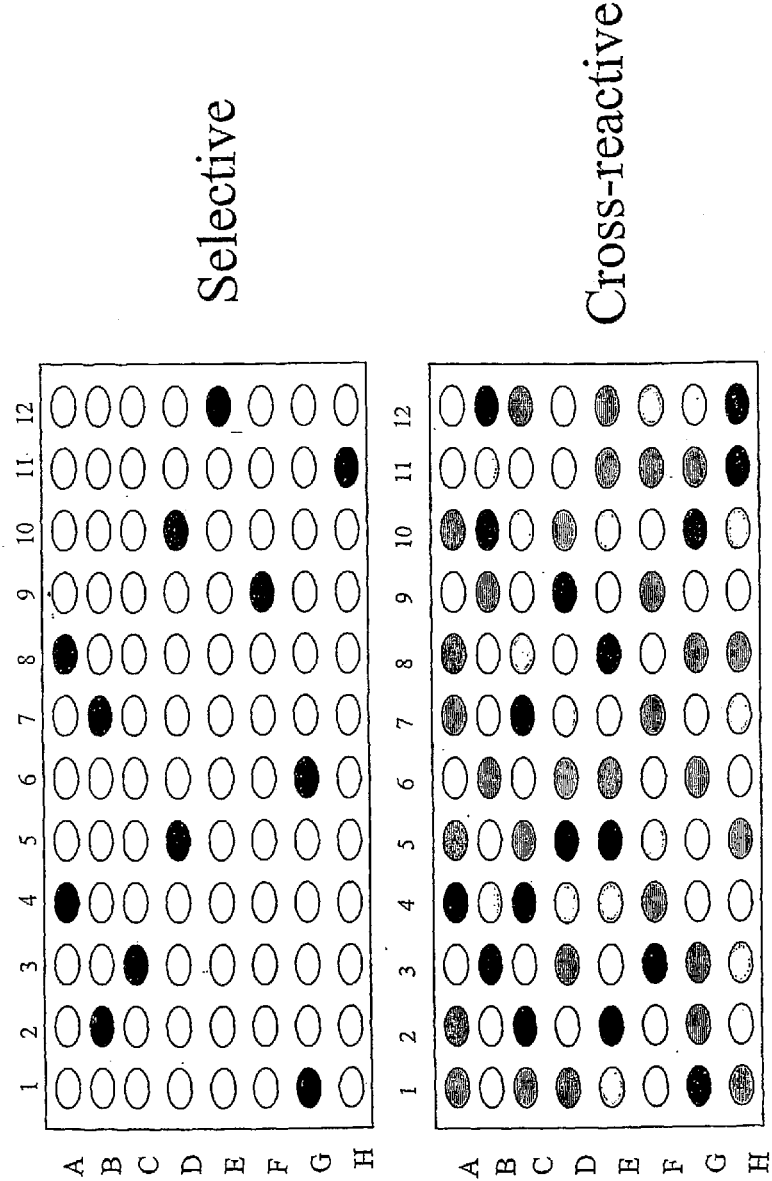
FIG. 1 depicts a microtiter plate as a sensor array, contrasting selective sensor arrays and cross-reactive sensor arrays.
Figure 7:
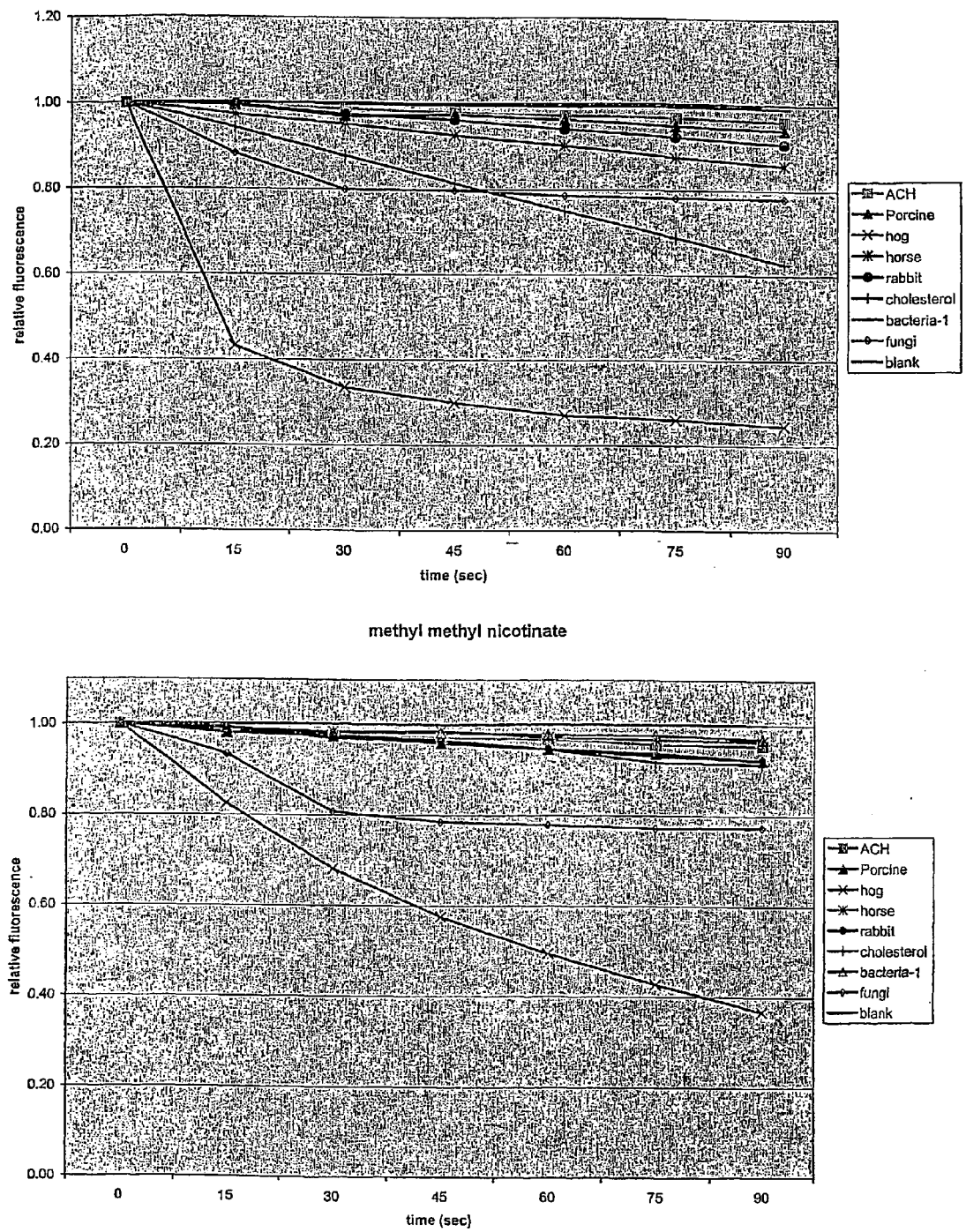
FIG. 7 depicts the relative fluorescence versus time for methyl 2-methyl glycidate and for methyl 6-methyl nicotinate.
Figure 8:
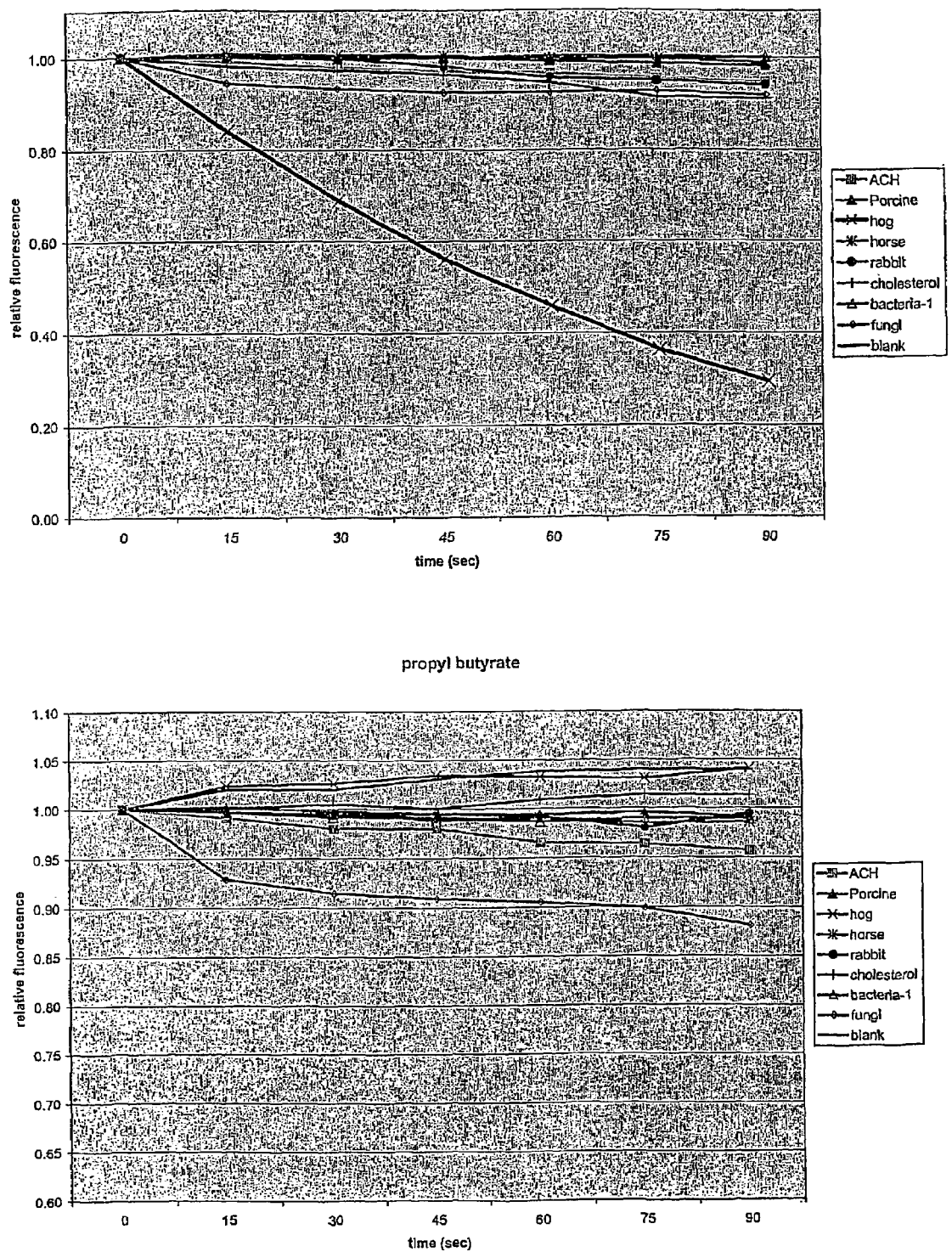
FIG. 8 depicts the relative fluorescence versus time for methyl nicotinate and for propyl butyrate.
Figure 9:
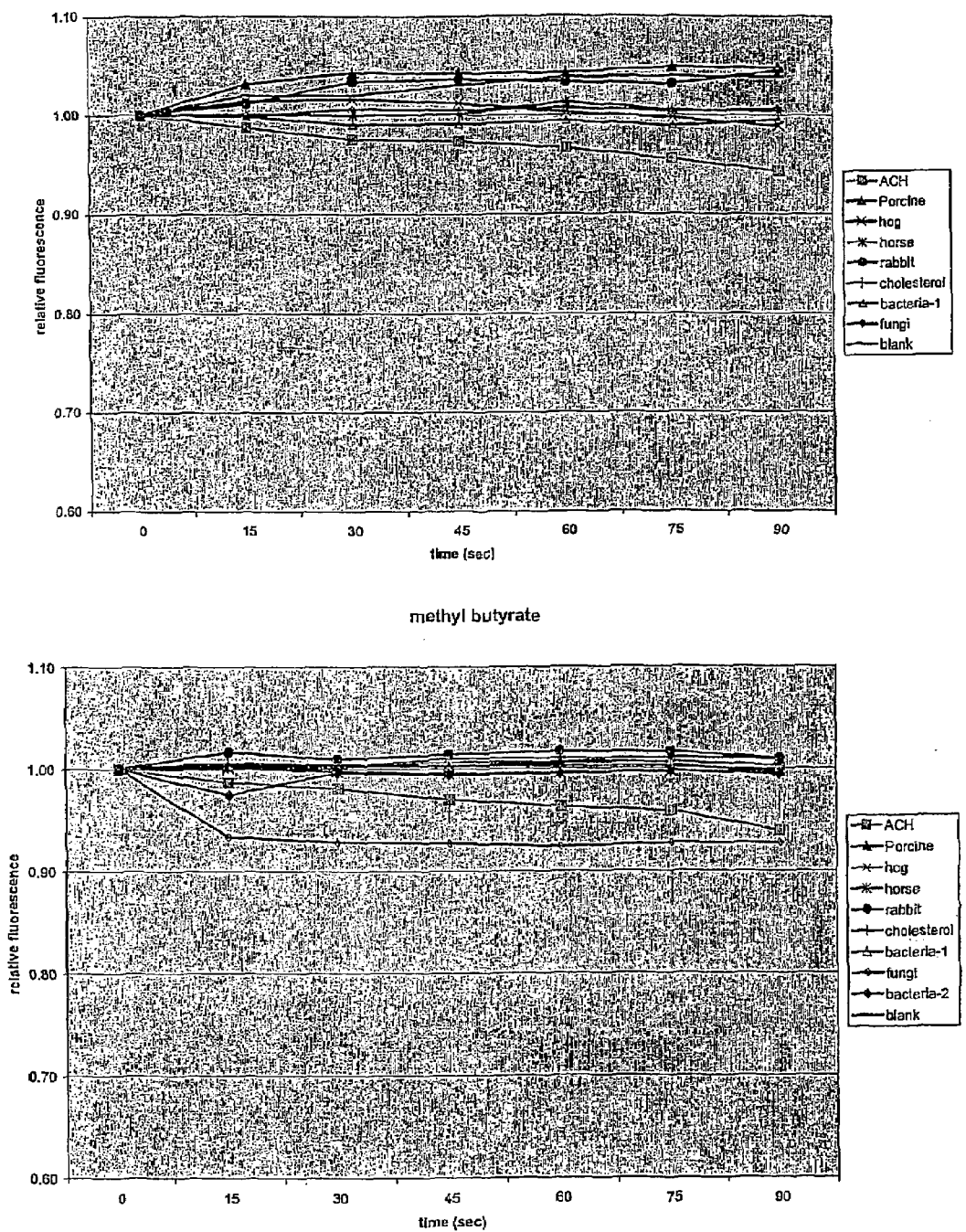
FIG. 9 depicts the relative fluorescence versus time for L-alanine methyl ester and for methyl butyrate.
Figure 10:
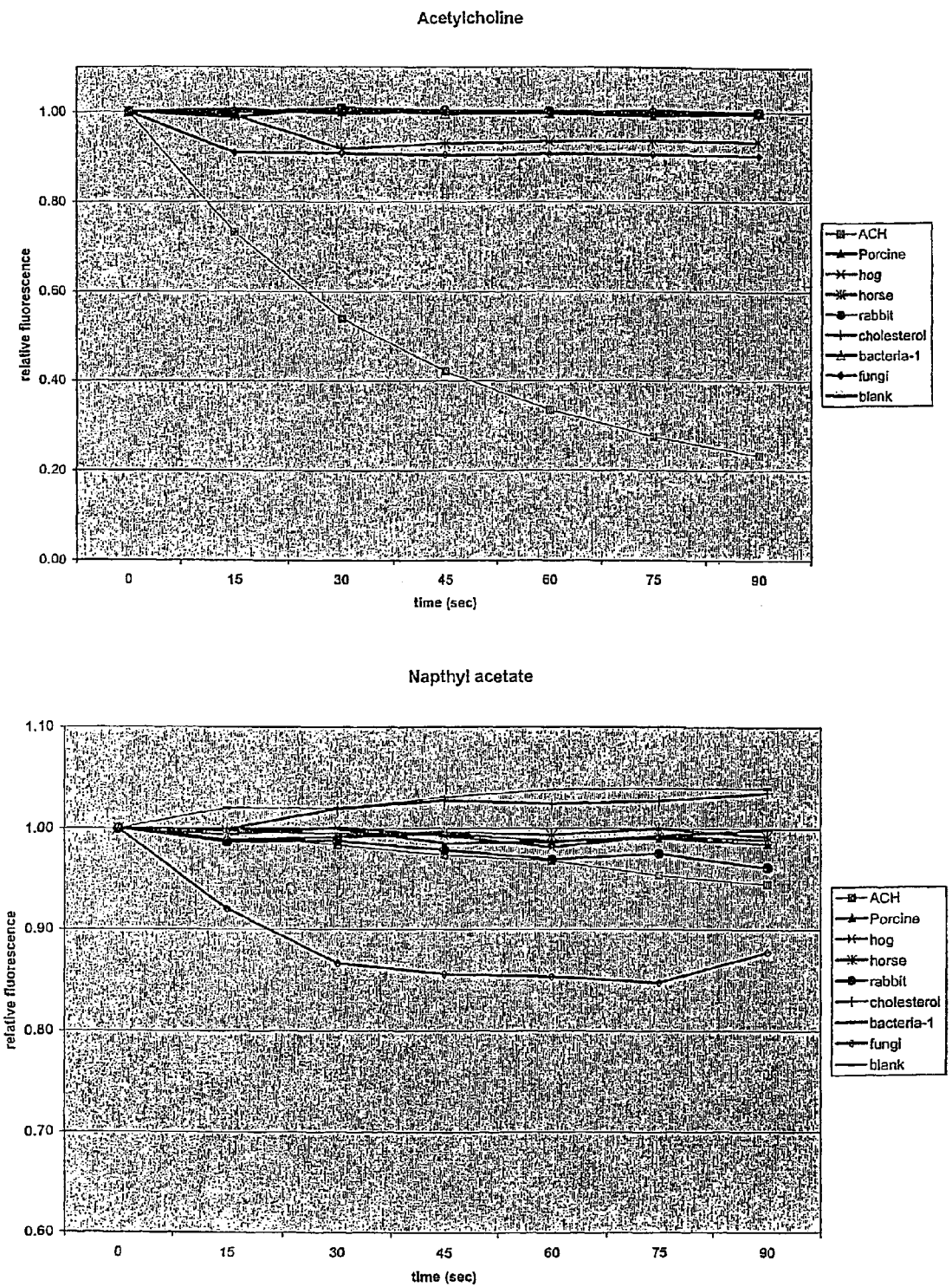
FIG. 10 depicts the relative fluorescence versus time for acetylcholine chloride and for napthyl acetate.
Figure 11:
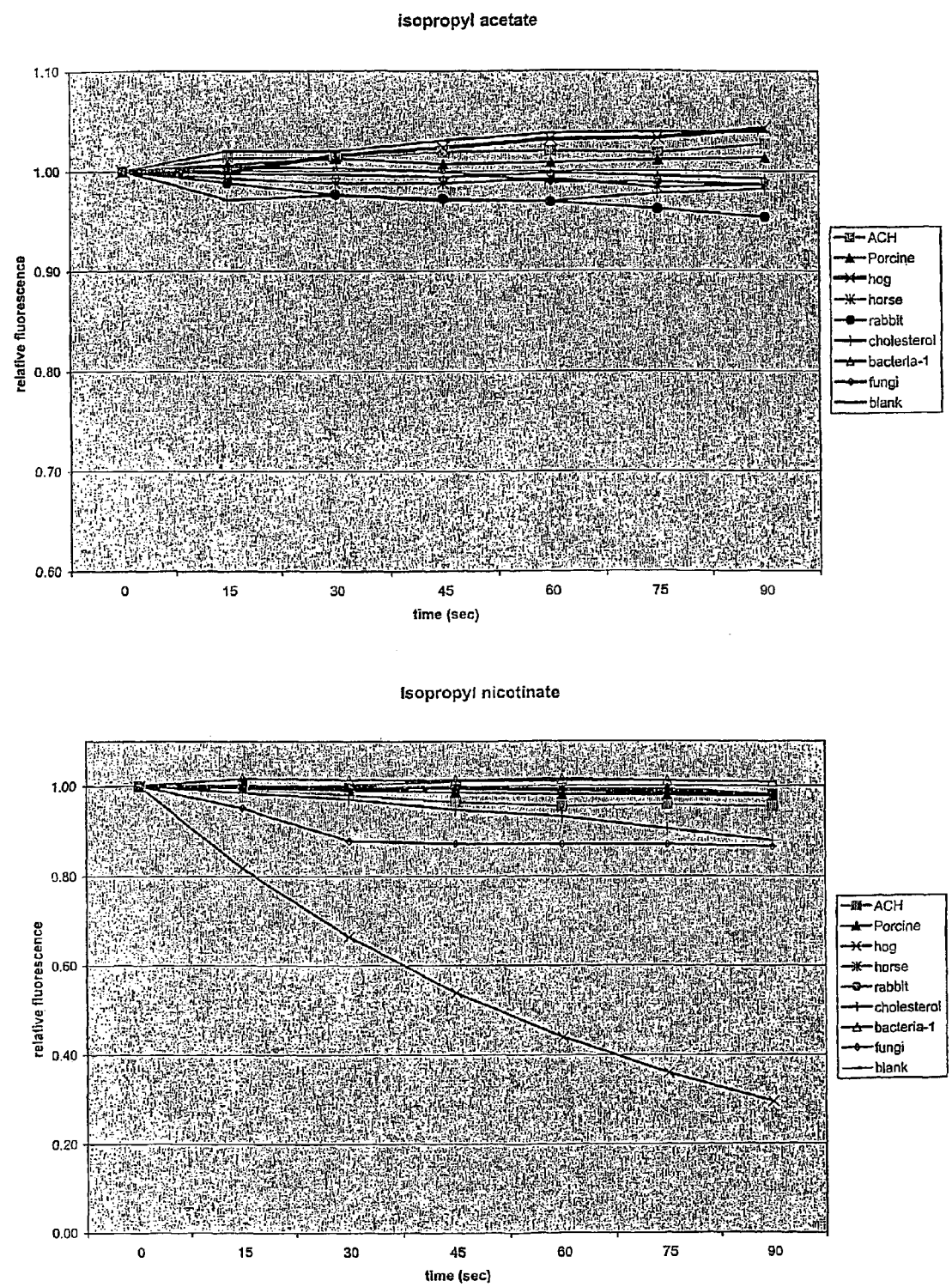
FIG. 11 depicts the relative fluorescence versus time for isopropyl acetate and for isopropyl nicotinate.
Figure 12:
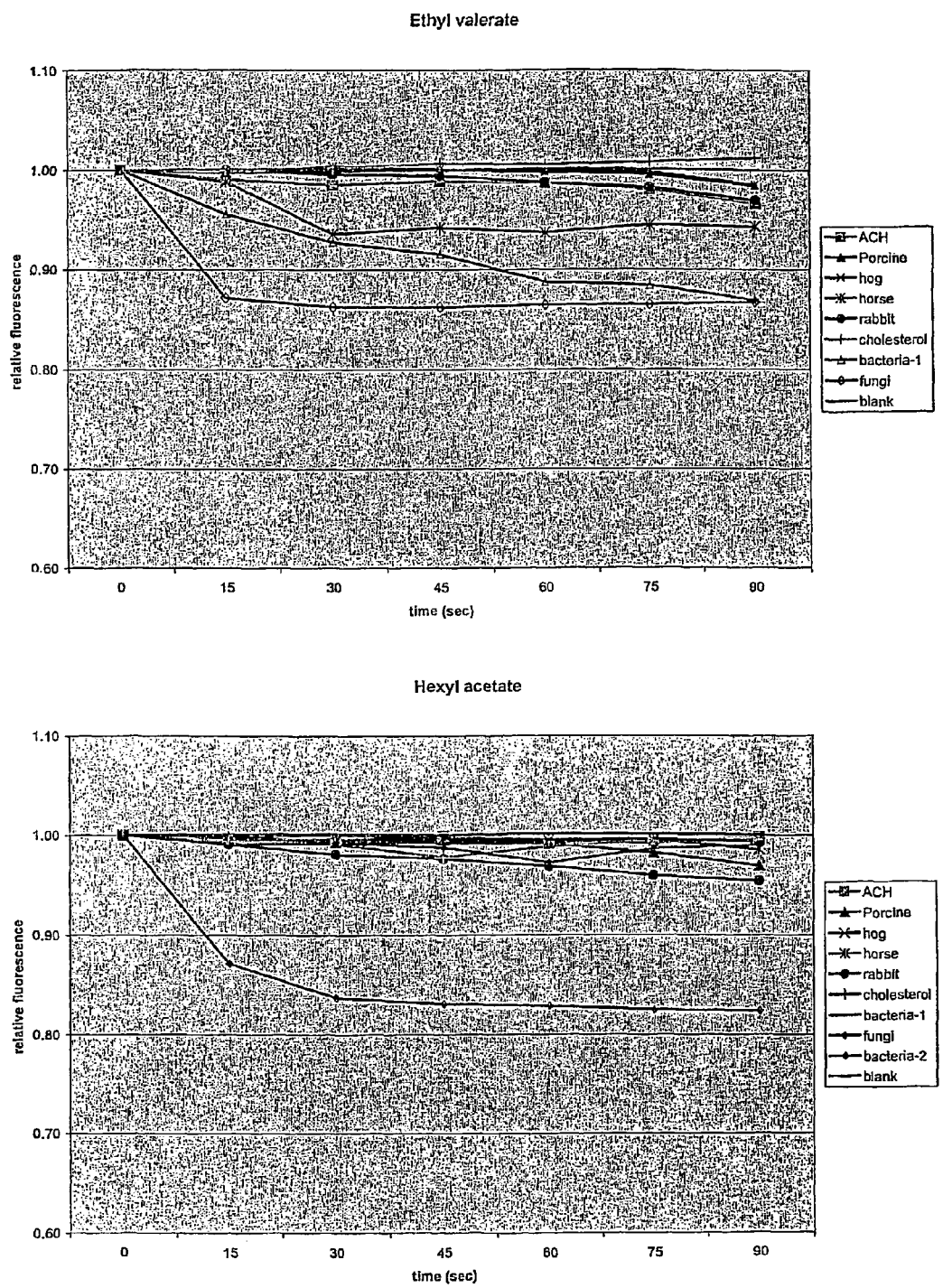
FIG. 12 depicts the relative fluorescence versus time for ethyl valerate and for hexyl acetate.
Figure 14:
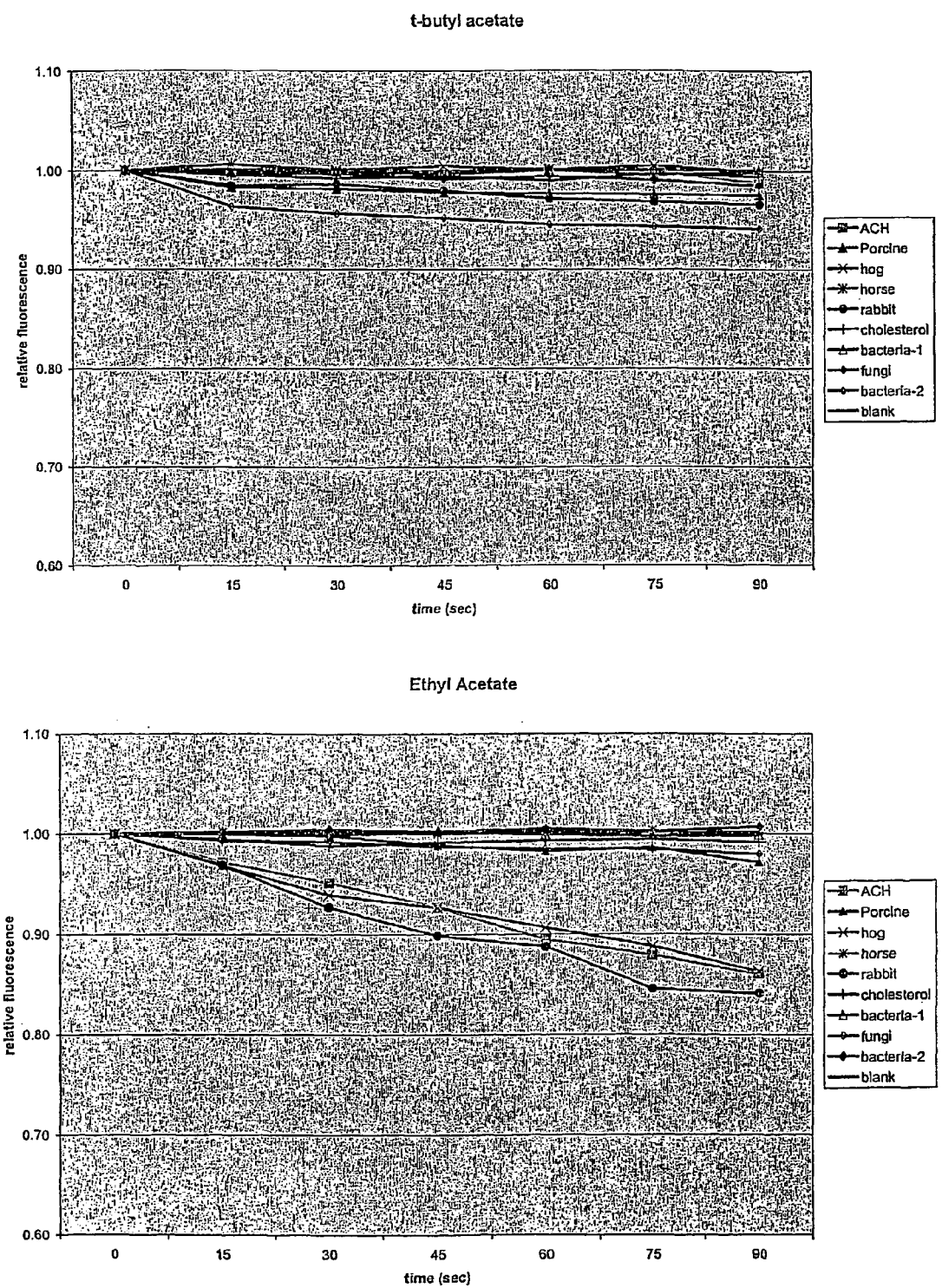
FIG. 14 depicts the relative fluorescence versus time for t-butyl acetate and for ethyl acetate.

As mentioned above, the development of more efficient sensors has been a challenging problem in analytical chemistry and, as a result, there has been continuous research and development in this important area. In recognition of this need, the present invention provides, for the first time, a sensor system for liquid analytes utilizing cross-reactive recognition elements. In general, the system of the present invention provides one or more cross-reactive recognition elements, wherein each of the one or more cross-reactive recognition elements is capable of interacting with more than one species of liquid analyte of interest, whereby each of the one or more cross-reactive recognition elements interacts in a different manner with each of the one or more species of liquid analytes of interest to produce a detectable agent for each analyte of interest. By "cross-reactive" it is meant, as used herein, that the recognition element utilized is capable of interacting with more than one species of analyte of interest, and additionally interacts with each of the more than one species in a different and uniquely identifiable manner (e.g., different rate of reaction, different reaction product produced, to name a few). In certain embodiments of the present invention, the detectable agent and/or change can be monitored or identified directly, wherein the information is processed for data acquisition and interpretation. In certain other embodiments of the present invention, a transducer agent is additionally provided, whereby the transducer is capable of relaying information about each detectable agent and/or change generated for each of the species of liquid analyte of interest, whereby the information is processed for data acquisition and interpretation.

Thus, in another aspect, the present invention provides a system for analysis comprising: 1) a sensor system as described above, wherein the sensor system optionally includes a transducer; and 2) a processing unit, which, after amplification of the primary signal, converts it into a familiar signal for subsequent data analysis. As used herein, the terms "transducer" or "energy transducer" are meant to include agents that are capable of relaying information about each detectable agent and/or change generated by the recognition event for each of the species of liquid analyte of interest. It will be appreciated that, in certain embodiments, two or more cross-reactive recognition elements will be required to analyze a solution of one or more analytes. In certain other preferred embodiments, however, only one cross-reactive recognition element will be required to analyze a solution of one or more analytes.

The present invention thus also provides a method for the analysis of analytes comprising: 1) contacting one or more analytes of interest with a cross-reactive sensor system as described above, and 2) analyzing the agents and/or change associated with the interaction. It will be appreciated that this agent and/or change is either analyzed directly, or with the help of a transducer. In certain embodiments, a processing unit (e.g., fluorescence detector, which is capable of detecting a fluorescent transducer) is utilized for the analysis of the agent and/or change associated with the interaction of the cross-reactive recognition element and the analytes of interest. It will also be appreciated that the method of the present invention may further include a chemoinformatic step, for example a step involving computational analysis, to sort, analyze, or process the data obtained.

In preferred embodiments of the inventive sensor system, the system for analysis, and the method of analysis, as described above, the cross-reactive recognition elements are provided in array format having a plurality of addresses, whereby the array comprises a plurality of addresses wherein two or more of the addresses contain the same type of cross-reactive recognition element. As shown in FIG. 1, the traditional sensor array system utilizing selective recognition agents is contrasted with the inventive cross-reactive sensor arrays. In this fashion, a "combinatorial sensor array" is generated, whereby a plurality of analytes can be detected by relatively few cross-reactive recognition agents.

It will be appreciated that the inventive sensors, in addition to being attached to array supports, can also be attached to solid supports, such as beads, and resins. As used herein, these terms are intended to include: beads, columns, plates, vials, tubes, slides, pellets, disks, strips, wafers, electrical leads, electrodes, wires, fibers, gels, or particles such as cellulose beads, controlled pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, or glass particles coated with hydrophobic polymer, to name a few. In general, the solid supports are made of any of a variety of materials, such as polymer, galss, silica, metal and the like. In certain embodiments, amino-functionalized or hydroxy-terminating beads are utilized to effect attachment of the sensors to the support. Those skilled in the art will further appreciate that attachment of any cross-reactive recognition element to any solid support merely requires choosing the appropriate cross-linker. Attachment of the cross-linker may occur during or after synthesis of the solid substrate.

Once attached to the solid support, the cross-reactive recognition elements are contacted with the analyte(s) of interest. In certain embodiments, the cross-reactive recognition element on the bead is contacted directly with the analyte. In other embodiments, the solid support containing the cross-reactive recognition element, e.g., the bead, is placed in array format having a plurality of addresses, whereby each address in the array contains one bead having an attached cross-reactive recognition element. In yet other embodiments, one or more beads having attached cross-reactive recognition elements are provided in array format having a plurality of addresses, whereby each address in the array contains more than one bead having an attached cross-reactive element. For example, once synthesized, the beads containing the cross-reactive recognition elements may be placed in complimentary wells of an etched optical imaging fiber Illumina (San Diego, Calif.).

Finally, as with the array described above, two or more of the addresses may further contain beads having the same type of cross-reactive recognition element. Alternatively, two or more of the addresses may further contain beads having different types of cross-reactive recognition elements. In yet another embodiment, each address contains a bead having attached to it a different cross-reactive recognition element. Placing the solid supports in an array format allows analysis of analytes that utilize multiple cross-reactive recognition elements simultaneously.

The present invention will be described in more detail below with respect to certain exemplary embodiments. It will be appreciated, however, that these embodiments are not intended to limit the scope of the present invention.

Exemplary Cross-Reactive Recognition Agents

It will be appreciated that a variety of cross-reactive recognition agents can be utilized in the present invention for the analysis of a variety of desired analytes or species of analytes. In particular, cross-reactive recognition agents are selected for their ability to interact with more than one analyte or species of analytes of interest, such that the cross-reactive recognition agent interacts in a different manner with each individual analyte of interest. As used herein, the term "interacts in a different manner" means that a distinct agent and/or change is produced upon interaction of the analyte and the cross-reactive agent, such that each distinct agent and/or change can be uniquely identified. Analytes and cross-reactive agents may interact in a different manner by producing agents (e.g., reaction products) at different rates, by producing agents having different chemical properties, or by inducing a detectable conformational change, to name a few.

It will be appreciated that the system of the present invention contemplates the use of any suitable cross-reactive recognition agent for the analysis of desired analytes. As discussed above, and as will become readily apparent below, suitable cross-reactive recognition agents comprise those agents that are capable of interacting in a different manner with each individual analyte of interest to produce a distinct agent and/or change that can be readily detected. It will be appreciated that, in certain embodiments, two or more cross-reactive recognition elements will be required to analyze a solution of analytes, because certain cross-reactive recognition elements will interact only with certain analytes in a solution and not others. In certain other preferred embodiments, only one cross-reactive recognition element will be required to analyze a solution of analytes, because the cross-reactive recognition element will be able to interact with each analyte to produce a unique agent and/or change that can subsequently be analyzed. As mentioned above, the inventive system is also preferably utilized in array format having a plurality of addresses, wherein two or more of the addresses contain the same cross-reactive recognition element for analysis of multiple analytes. In preferred embodiments, one cross-reactive recognition agent per address is utilized, however, it will also be appreciated that, in other embodiments, more than one cross-reactive recognition agent per address can be utilized for analysis. One example of such a system utilized for selective recognition agents includes a sequential microenzymatic assay of cholesterol, triglycerides, and phospholipids in a single aliquot. See, Nanjee et al., *Clinical Chem*, 1996, 42, 915. Additionally, in another example, the sensing of acetylcholine by a tricomponent-enzyme layered electrode using Faradaic Impedance Spectroscopy, cyclic voltammetry and microgravimetric quartz crystal microbalance transduction methods is described in Alfonta et al., *Anal. Chem.*, 2000, 72, 927.

Certain exemplary cross-reactive recognition agents that can be utilized in the present invention include, but are not limited to, cross-reactive enzymes, cross-reactive receptors, cross-reactive transition metals, cross-reactive ligands for transition metals, and cross-reactive synthetic catalysts, to name a few. For example, certain cross-reactive enzymes that can be utilized include, but are not limited to, esterases, hydrolases, isomerases, lysases, transferases, oxido-reductases, and ligases. Such enzymes can be utilized to detect and/or analyze a variety of reagents including, but not limited to amino acids (using L-amino acid oxidase, D-amino acid oxidase), alcohols (using alcohol dehydrogenase, alcohol oxidase), sugars, esters (using esterases), and proteins (using proteases).

In certain embodiments of the present invention, cross-reactive esterases are utilized, whereby the esterases are capable of hydrolyzing different esters (analytes) at different reaction rates, thus producing desired products at different rates. The hydrolysis and production of reaction products can then be monitored over time to produce distinct patterns for different analytes. As depicted below in Equation 1, esterases hydrolyze esters to produce alcohols and carboxylic acids:

Equation 1

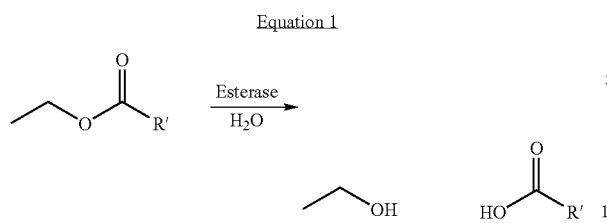

As depicted, the enzyme reacts with the analyte (ester) causing a change in pH (via production of the carboxylic acid). The change in pH over time (due to differing reaction rates with different analytes) can then be monitored (in one example, by using pH sensitive fluorescent dyes) to produce distinct patterns for specific analytes. As described in the examples below, certain exemplary esterases for use in the present invention include, but are not limited to, esterase from rabbit liver, esterase from porcine liver, acetylcholine esterase from electrophorous electricus, cholesterol esterase from hog pancrease, esterase from hog liver, esterase from horse liver, esterase from *mucor miehei*, esterase from *bacillus* sp., and esterase from *bacillus thermoglucosidasius*.

In certain other embodiments, the cross-reactive recognition element is an agent that is capable of undergoing a cross-reactive biorecognition event. For example, the cross-reactive biorecognition event may be based on a catalytic conversion with an enzyme or organelle acting as a catalytic agent transforming an agent or a substrate into a measurable product. Alternatively, the analyte may only take part in a binding event based upon an antibody or receptor. As discussed above, such agents are cross-reactive, that is they are capable of interacting with different species of analytes to produce distinct agents and/or changes. It will also be appreciated by one of ordinary skill in the art that so-called artificial receptors can be utilized in the present invention.

Thus, in certain embodiments, the present invention contemplates the use of receptors as cross-reactive recognition agents, including, but not limited to, chemosensors, phosphorescent chemosensors, cryptands, carcerands, hemicarcerands, hemicarceplexes, carceplexes, spherands, hemispherands, cryptahemispherands, coraplexes, velcraplexes, cyclophanes, cyclic oligonucleotides, cyclic ureas, cyclic peptides, nanotubes, discrete aggregates, clefts and polyaza clefts, macrolactams, macrobicyclics, macrocyclics, macrotricyclics, calix[n]arenes, crown ethers, cyclodextrins, hemispherands, cages, chlorophyls, cavitands, cavitand dimers, catenanes, grids, polymers, double and triple helicates, porphryns, viruses, self-assembling enzymes, DNA, RNA, peptides, proteins, micelles, fibers and discs. Each of these agents, as described herein, and equivalents thereof, as utilized in the inventive system, is capable of interacting with one or more analytes of interest and producing a detectable agent and/or change that uniquely identifies each of the one or more analytes. In but one example, a broadly selective receptor (e.g., cross-reactive) could be monitored for analyte binding by a change in fluorescence (a fluorescent probe is utilized to monitor the binding of the guest), FTIR (fourier transform infared spectroscopy), NMR (nuclear magnetic resonance spectroscopy), vapor pressure osmometry, or any other suitable method to monitor a change in binding.

It will be appreciated by one of ordinary skill in the art that a specific cross-reactive recognition agent can selected to tailor the inventive system to the specific analytes being analyzed. Exemplary systems for use in the inventive cross-reactive sensor are described in the following: "Handbook of Biosensors and Electronic Noses: Medicine, Food, and Environment", Kress-Rogers, Ed., CRC Press, New York, 1997; "Biosensors: Fundamentals and Applications" Turner, A.; Karube, I.; Wilson, G., Eds., Oxford University Press, Oxford, 1987; and "Introduction to Bioanalytical Sensors", Cunningham, A., Ed., John Wiley & Sons, Inc., New York, 1998, and the entire contents of each reference are hereby incorporated by reference.

Detection of Analytes

After interaction with the cross-reactive recognition agent to produce a distinct agent and/or change, this agent and/or change is capable of either being monitored or analyzed directly, or a transducer element agent may also be employed to facilitate analysis. As used herein, the terms "transducer" or "energy transducer" are meant to include agents that are capable of relaying information about each detectable agent and/or change generated by the recognition event for each of the species of liquid analyte of interest. It will be appreciated by one of ordinary skill in the art that a variety of transducer agents can be utilized, and that transducer agent is selected for the ability to relay information about the agent and/or change generated by the cross-reactive recognition event.

For example, as discussed above, the hydrolysis of esters can be detected by pH sensitive dyes (due to the production of protons). Additionally, amino acids can be detected using L-amino oxidase or D-amino acid oxidase using a pH indicator or $O_2$ indicator; alcohols can be detected using alcohol dehydrogenase or alcohol oxidase using a pH sensor, NADH-indicator, or $O_2$ indicator; and proteins can be detected using proteases and a pH sensor or competition assay with a protein that is reactive and carries covalently attached dye molecules which increase in fluorescence as the reaction progresses.

In general, suitable transducers are selected from the group consisting of electrochemical transducer, optical transducer, thermal transducer, and acoustic transducer, to name a few. In certain preferred embodiments, electrochemical transducers are utilized, preferably those involving an energy transduction mode selected from the group consisting of amperometric, conductimetric, impedimetric, potentiometric, and potentiometric stripping analysis. In other preferred embodiments, the optical transducers are utilized, preferably those involving an energy transduction mode selected from the group consisting of absorbance, chemiluminescence, electrogenerated chemiluminescence, fluorescence, fluorescence lifetime, fiber optic waveguides, near-field microscopy, near-field spectroscopy, near-infared, planar waveguides, surface enhanced raman, and surface plasmon resonance. In certain particularly preferred embodiments of the present invention, the optical transducer comprises a pH sensitive dye, most preferably pH sensitive dyes selected from the group consisting of fluorescein, carboxyfluorescein, SNAFL, SNARF, LysoSensor Green DND-189, Oregon Green, NERF, LysoSensor Yellow/Blue DND-160, HPTS (pyranine), BCECF, BCPCF, and Bodipy, or oxygen sensitive dyes comprises $Ru(bipy)_3Cl_2$, $Ru(4,7\text{-diphenyl-1},10\text{-phen})_3(Cl)_2$ and trans-1-(2'-methoxyvinyl)pyrene. Other fluorescent probes can also be utilized as transducer agents according to the present invention, many of which are described in "Molecular Probes: Handbook of Fluorescent Probes and Research Chemicals", Seventh Edition, Richard P. Haughland, 1999, the entire contents of which are hereby incorporated by reference. As depicted in the examples described below, the use of pH sensitive fluorescent dyes enables the detection of relative fluorescence over time and thus the differences in reaction rates can be measured, thus uniquely identifying desired analytes (for examples, esters). As depicted in FIGS. 2 and 3, five substrates initially tested are distinguishable by two esterases using principal component analysis. Additionally, FIG. 3 depicts distinguishable regions corresponding to specific analytes. In still other embodiments, acoustic transducers are utilized preferably those involving an energy transduction mode selected from the group consisting of acoustic plate mode, flexural plate mode, surface acoustic wave, surface transverse wave, and thickness shear mode. In yet other embodiments thermal transducers are utilized, which preferably employ atic or heat transduction.

These and other suitable transducers are more generally described with respect to particular systems in "Introduction to Bioanalytical Sensors", A. J. Cunningham, John Wiley & Sons, New York: 1998, the entire contents of which are hereby incorporated by reference. Additionally, this reference describes the methods of analysis and data interpretation for specific transducers for a variety of systems, each of which can be adapted to the present invention. Thus, the present invention additionally provides a system for analysis comprising 1) the sensor system described in detail above, and 2) a processing unit for the acquisition and analysis of data In certain preferred embodiments, this processing unit is capable of measuring measuring fluorescence. It will be appreciated that any processing unit may be utilized that is appropriate for the particular transducer employed, or, for the case of direct analysis, a processing unit that is capable of processing and interpreting data directly from the agent and/or change produced upon interaction of the cross-reactive recognition element and the analyte to provide a familiar readout (e.g. ppm, pH, relative fluorescence, to name a few).

Furthermore, the present invention also provides a method of analysis comprising: 1) contacting one or more analytes of interest with a cross-reactive sensor system as described above, and 2) analyzing the agents and/or change associated with the interaction. It will be appreciated that this agent and/or change is either analyzed directly, or with the help of a transducer. In certain embodiments, a processing unit (e.g., fluorescence detector can be used to monitor relative fluorescence over time) is utilized for the analysis of the agent and/or change associated with the interaction of the cross-reactive recognition element and the analytes of interest. One example of a technique for analysis that can be utilized in the method of the present invention can be found in "Identification of Multiple Analytes Using an Optical Sensor Array and Pattern Recognition Neural Networks" *Anal. Chem.* 1997, 69, 4641–4648, the entire contents of which are hereby incorporated by reference. One of ordinary skill in the art will also realize that, in addition to a step of processing using a processing unit, an optional step may include further data analysis, e.g., using a chemoinformatic step (for example, via computational analysis) to sort, process, or further analyze the data obtained.

Uses

As will be appreciated by one of ordinary skill in the art, the ability to detect desired liquid analytes is very useful in a range of disciplines. For example, the inventive system may be utilized for medical/biochemical applications, specifically for the analysis of such agents, including, but not limited to, drugs (for example, cocaine), glucose, blood gas, neurotransmitters (for example, acetylcholine), DNA sequence, pH and electrolytes. Other uses include, but are not limited to, environmental analysis (for the analysis of such harmful agents as PCBs, pesticides, heavy metals, herbicides) and bioprocessing technology (for the analysis of pH, sugars, Mab Production, dissolved gases, recombinant DNA processes, alcohols). For example, industries involved in pharmaceuticals, food processing and recombinant DNA technology need effective sensors for monitoring various processes. One of ordinary skill in the art will realize that the inventive system may be utilized in a variety of disciplines requiring analysis of liquid analytes, and are not limited to those applications discussed above.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and the equivalents thereof.

EXEMPLIFICATION

Example 1

Enzyme-Based Sensor Array

As described above, the present invention provides an inventive sensor system that utilizes cross-reactive recognition elements, wherein each of the cross-reactive recognition elements is capable of interacting with more than one species of liquid analyte of interest, whereby each of the one or more cross-reactive recognition elements reacts in a different manner with each of the one or more species of liquid analytes of interest to produce a detectable agent for each analyte of interest. This detectable agent can then be analyzed directly, or a transducer agent can also be provided to relay the chemical information for analysis. In one embodiment of the present invention, an enzyme-based sensor array is utilized, as will be described in more detail below.

The present example utilizes a cross reactive sensor array that is generated from a group of esterases that react to a broad range of ester analytes, where each ester elicits a response from multiple esterases. As described herein, one advantage to the cross-reactive sensor array is that only a few sensors are needed to distinguish a wide variety of analytes since a pattern recognition program can differentiate the many combinations of responses. The present example further illustrates the inventive approach, which employs analyte-related enzymes that all catalyze the same type of reaction, but have different and somewhat overlapping specificities. In this way, the specificity of the sensor array is restricted to a certain class of substrates. We utilize the cross-reactivity of enzymes in combination with a pattern recognition scheme to identify the specific molecule present.

Enzymes catalyze reactions required for biological processes and exhibit intrinsic specificity. In their recognition of substrates, many enzymes are selective; for example, L-glutamate oxidase oxidizes only L-glutamate. Other enzymes are class-selective, such as L-amino acid oxidase, which catalyzes the oxidation of a range of L-amino acids with varying kinetics. The incorporation of class-selective enzymes into an enzymatic array bioassay format exploits the enzyme's inherent cross-reactive nature.

Esterases catalyze the hydrolysis of esters to carboxylic acids (see equation below).

Equation 2

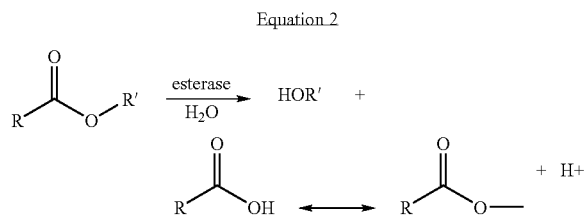

A fluorescent pH indicator, fluorescein, was added to the reaction mixture to measure the change in acidity resulting from the hydrolysis reaction in a 96-well microtiter plate format. The fluorescence response was monitored over time to give a temporal pH-induced fluorescence pattern. Esterases were utilized for these initial demonstrations of the enzymatic array assay because they are commercially available, relatively stable, and react with a wide range of esters. Esterases have been used to test ester chirality (Janes et al., *Chem. Eur. J*, 1998, 4, 2324) and as synthetic tools for efficiently hydrolyzing a variety of esters (Ohno et al., Org. React, 1989, 37, 1).

General Procedure for Enzyme-Based Sensor Array:

In but one example of an inventive sensor array system, a cross-reactive esterase is utilized as the recognition element.

First, solutions of desired substrates (certain exemplary substrates are depicted in FIGS. 4 and 5) were made from 100 mM of substrate in $CH_3CN$ (or buffer, depending on the solubility of the ester). The analyte concentration was chosen to be at most one-fifth of the Michaelis constant (kM) for the esterases. All solvents and substrates were purchased from Aldrich, Sigma, and Fluka Chemical Companies and used as received.

All substrates were purchased from Sigma or Fluka. Subsequently, a solution having the following components is generated:
- 420 µL of 100 mM substrate in $CH_3CN$;
- 470 µL $CH_3CN$;
- 600 µL of a fluorescein dye solution in buffer; and
- 10510 µL 0.01 mM Phosphorous Buffer Solution to generate:
- 12000 µL total substrate solution Second, enzyme solutions were assembled to the desired activity levels as shown below and exemplary enzyme based biosensors are listed below and were purchased from Sigma and Fluka:
- Esterase from Rabbit liver
- Esterase from Porcine liver
- Acetylcholine Esterase from Electrophorus electricus
- Cholesterol Esterase from Hog pancrease
- Esterase from Hog liver
- Esterase from Horse liver
- Esterase from *Mucor miehei* (denoted fungi)
- Esterase from *Bacillus* sp. (denoted bacteria-1)
- Esterase from *Bacillus thermoglucosidasius* (denoted bacteria-2)

Additionally, depending on the activity of the above esterases, the solutions were assembled as such:

| | | |
|---|---|---|
| Cholesterol | 35 U/mg | 5.65 mg/mL |
| Acetylcholine | 850 U/mg | 0.073 mg/mL |
| Bacillus sp. | 0.1 U/mg | 6.0 mg/mL |
| Bacillus th. | 0.1 U/mg | 6.0 mg/mL |
| Hog liver | 220 U/mg | 1.3 mg/mL |
| Horse liver | 0.7 U/mg | 2.5 mg/mL |
| Mucor | 1.0 U/mg | 5.7 mg/mL |
| Porcine | 150 U/mg | 1 µL/mL |
| Rabbit | 80–120 U/mg | 2 µL/mL |

The microtiter plate assay provides a rapid and reproducible system to measure the hydrolysis reactions. In the present example, the microtiter plate assay contained the nine esterases in different columns and the ester analytes in the different rows. Each esterase catalyzed hydrolysis reaction was addressed individually to monitor the kinetics by scanning each well independently. After preparation of the desired solutions, to the microtiter plate was first pipetted (using a pipetman) 100 µL of the substrate solution into each well. Then, a 5 µL aliquot of the enzyme solution was pipetted into the well, resulting in a volume in the 96 well microtiter plate (per well) of 105 µL, which equals to 29 µM substrate and 30–0.04 µg of enzyme, or at most a concentration of substrate of one-fifth the Km. The plate was allowed to shake for 10 seconds before the first reading. The reader reads 15 second intervals while shaking before each read. The plate was monitored for 90 seconds by a Molecular Devices, Spectra Max Gemini, fluorescence microtiter plate reader. The reader scans each row and column of the microtiter plate reading each well individually. Therefore, each enzyme was monitored individually and the enzyme's kinetics were measured at the same point in time. The reader displays the resulting changes in fluorescence in graph form, the slopes of which are used for the computational analysis program, MATLAB. The MATLAB program analyzes the individual interactions and separates them into clusters, which can indicate the ability of the sensor to distinguish the analytes.

The nine lyophilized esterases (Sigma and Fluka) were used as received and chosen based on their availability and wide range of specific activities. Twenty-three esters, ranging from simple aliphatic esters to multi-functional chiral esters, were chosen as analytes. Exemplary analytes include
- Ethyl propionate (EP)
- Ethyl benzoate (EB)
- Ethyl valerate (EV)
- Ethyl acetate (EA)
- Ethyl butyrate (BA)
- Propyl butyrate (PB)
- Isopropyl nicotinate (IN)
- Isopropyl acetate (IA)
- Methyl 2-methyl butyrate (MMBU)
- methyl butyrate (MBU)
- Methyl benzoate (MB)
- Methyl 2-methyl glycidate (MMG)
- Methyl nicotinate (MNI)
- Methyl 6-methyl nicotinate (MMNI)
- Methyl cyclohexane carboxylate (MC)
- L-alanine methyl ester (LM)

D-alanine methyl ester (DM)
t-butyl acetate (TA)
Hexyl acetate (HA)
2-naphthyl acetate (NA)
Acetylcholine chloride (AC)
Phenyl acetate (PA)
Propyl acetate (PRA)

The esters vary in the placement of functional groups close to the reaction center and include representatives ranging from methyl, ethyl and propyl esters, as well as acetates.

Figure 17:
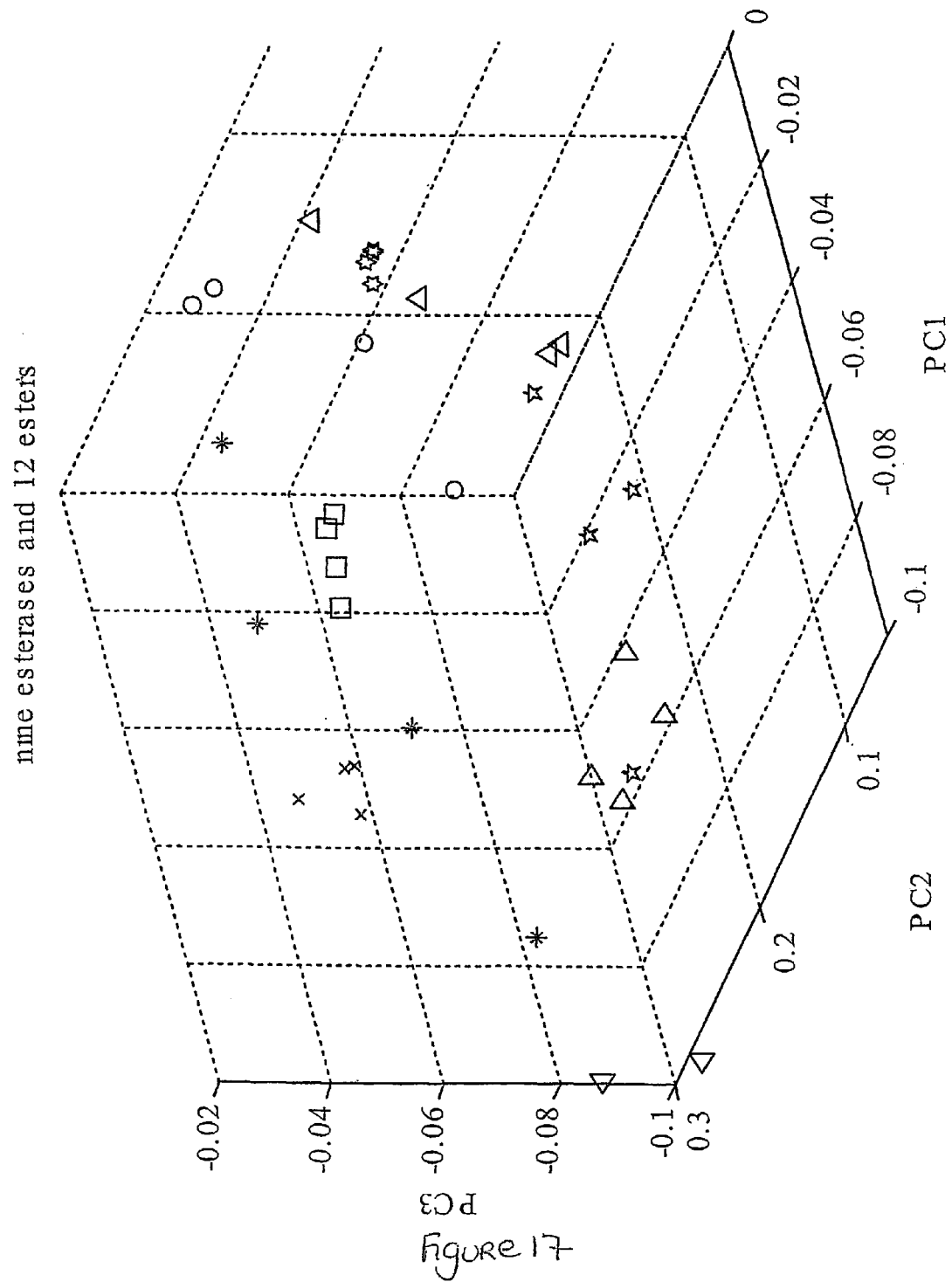
FIG. 17 depicts the three-dimensional principal component analysis for nine esterases and twelve esters.
Figure 18:
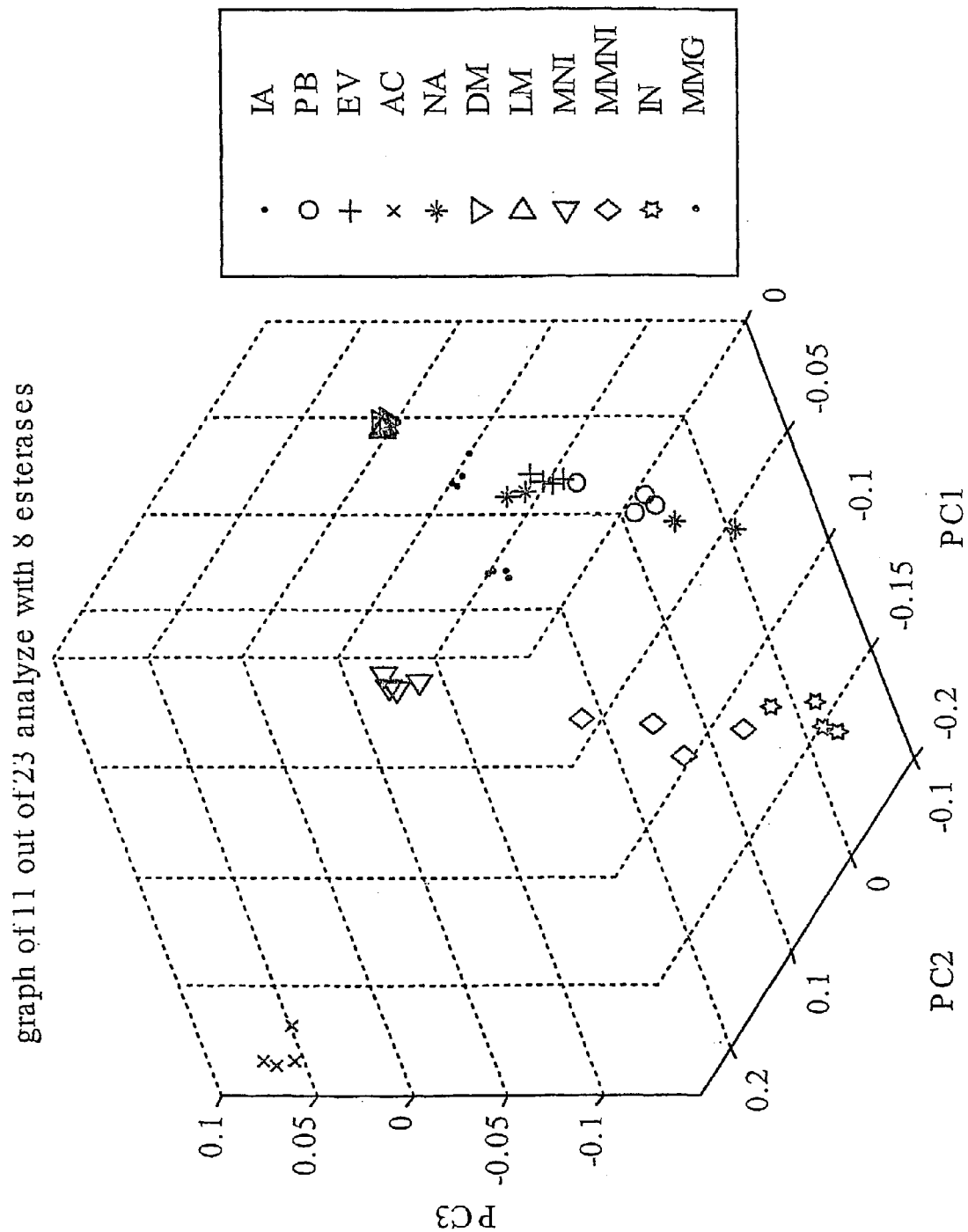
FIG. 18 depicts the three-dimensional principal component analysis for eleven esters and eight esterases.
Figure 19:
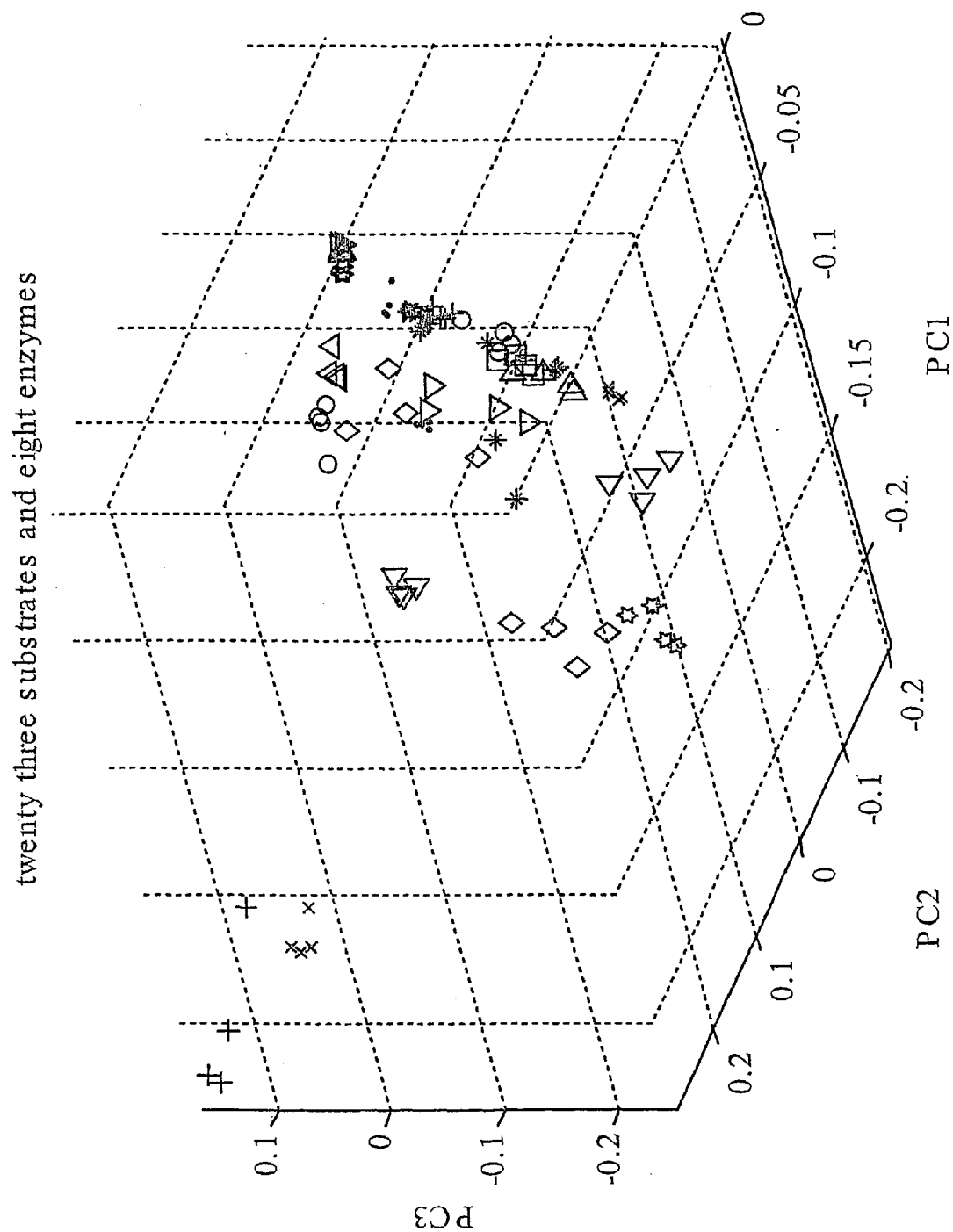
FIG. 19 depicts the three-dimensional principal component analysis for twenty-three substrates and eight enzymes.
Figure 81:
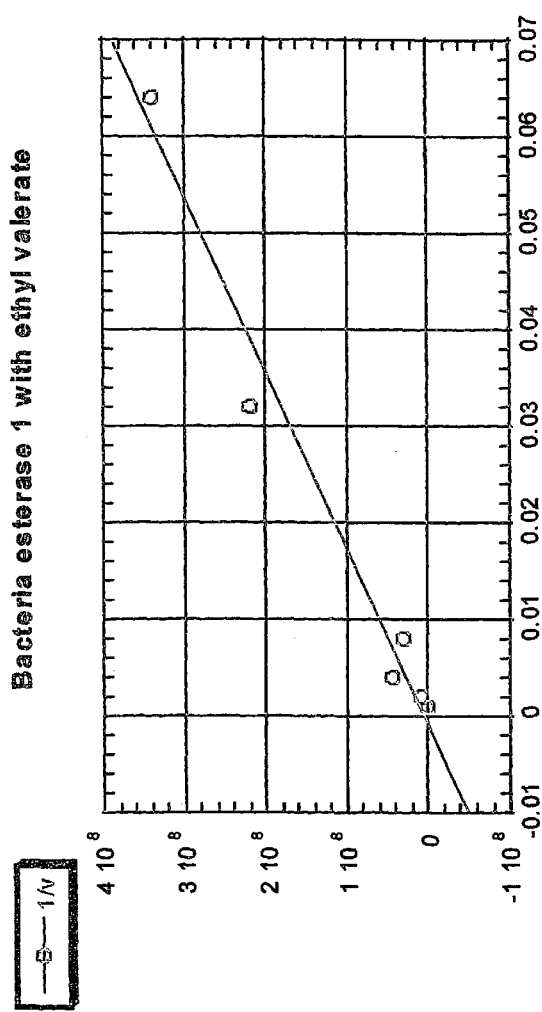

FIGS. 6–16 depict the relative fluorescence versus time for exemplary substrates (FIGS. 4 and 5) upon interaction with different types of cross-reactive esterases. Furthermore, FIGS. 17–19 depict the principal component analysis for different sets of esterases and analytes of interest, establishing distinguishable regions for specific analytes, allowing identification of the specific analytes.

The differing hydrolytic susceptibility of the esters to the esterases resulted in reactivity rate patterns, which were used to distinguish the esters. Among all of the esters, phenyl acetate (PA) is hydrolyzed the fastest. These patterns of reactivity provide a means to distinguish PA from other substrates.

Figure 26:
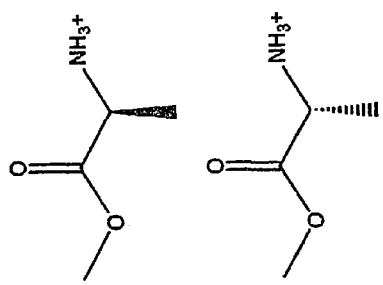
FIG. 26 depicts the chemical structure of two esters, L-alanine methyl ester (LM) and D-alanine methyl ester (DM), and highlighted regions of the confusion matrix of FIG. 24 showing the actual vs. the calculated identity of each ester of based on reaction rates with nine different esterases.

Of the nine esterases examined, acetylcholine esterase hydrolyzes all twenty-three esters. Rabbit esterase reacts with all of the esters except the simple aliphatic esters. In order to exemplify the discriminating ability of the current system, D-alanine (DM) and L-alanine (LM) methyl esters were included as analytes. DM and LM are both hydrolyzed by acetylcholine esterase and bacteria 1 esterase, while bacteria 2 esterase, hydrolyzes only LM and not DM. These differences in reactivities provide a "fingerprint" of each ester. (See FIG. 26).

The sensitivity of the assay is further illustrated in FIGS. 20 and 21. The reaction rates of bacteria esterase 1 with ethyl valerate and methyl methyl nicotinate are quite distinguishable, having Vmax and Km values of $2\times10^{-7}$ Ms$^-$and 1 mM and $4\times10^{-7}$ Ms$^{-1}$ and 2.6 mM, respectively.

The esterase array was further tested for assay reproducibility. The hydrolysis reaction slopes of three esters, PA, methyl butyrate (MB), and ethyl butyrate (BA) were measured initially and after three months. The initial slope range and standard deviation for the three esters with acetylcholine esterase were PA $(-1.4\pm0.2)\times10^2$, MB $(-1.3\pm0.01)\times10^2$, and BA $(-2.9\pm1.6)\times10^3$ respectively; after three months the slopes were PA $-1.5\times10^3$, MB $-1.3\times10^2$, and BA $-3.2\times10^2$. The slopes, therefore, lie within the initial ranges after three months. FIG. 22 further illustrates this point by showing that the slope of the reaction in fluorescence units/time does not vary from experiment to experiment over a number of days.

Figure 23:
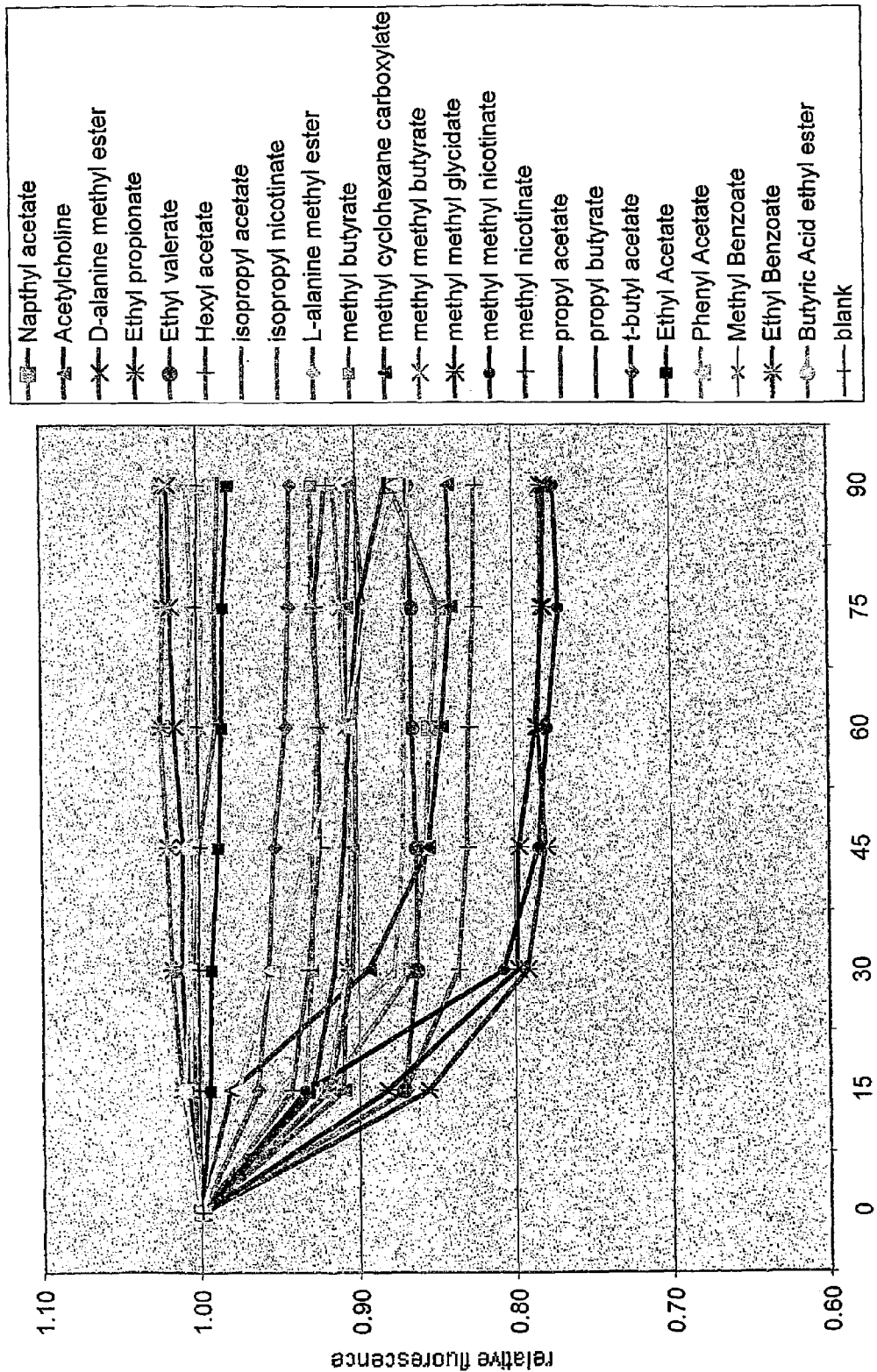
FIG. 23 depicts the reaction rate curves of esterase from *Mucor miehei* (denoted fungi) with twenty-three different ester analytes.

The hydrolysis reaction initial slopes were used as input for principal component analysis (PCA). The individual interactions were analyzed and separated into clusters for which the tightness of the clusters indicates the array's ability to distinguish the analytes. By combing the response patterns of all nine esterases for the twenty-three analytes from four independent assays, a confusion matrix was compiled from the PCA data. The rate curves for the esterase from fungi are shown in FIG. 23. The confusion matrix compares the calculated versus actual ester identity and is 90% correct using 98% of the data's variance.

TABLE 1

The confusion matrix results: column number indicates number of esters identified incorrectly. Abbreviation in parenthesis indicates the PCA identification of the incorrect ester.

| 0 | 1 | 2 | 3 | 4 |
|---|---|---|---|---|
| EA; PA; MB; IN; MNI; EV; MMG; MBU; AC; IA; PB; EB; MC; EP; DM; LM, MMNI; HA; MMBU | NA (IA) | PRA (DM(2); TB (EV; LM) | | BA (EA(2); MMBU; MBU) |

Figure 25:
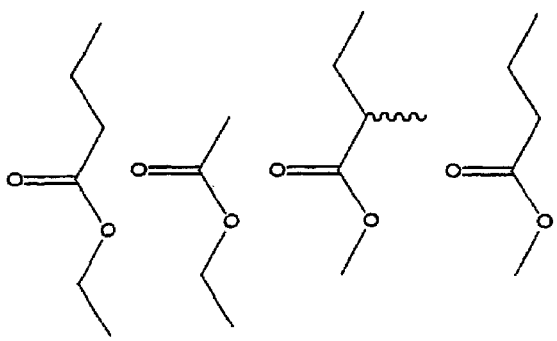
FIG. 25 depicts the chemical structure of four esters, ethyl acetate (EA), ethyl butyrate (BA), methyl 2-methyl butyrate (MMBU), and methyl butyrate (MBU), and highlighted regions of the confusion matrix of FIG. 24 showing the actual vs. the calculated identity of each ester based on reaction rates with nine different esterases.

As seen in Table 1, four of the twenty-three esters were misidentified. For three of the four misidentified esters, no clear structural basis exists to cause the esters to be misclassified in PCA, however, their hydrolysis reaction slopes are similar. The fourth ester, BA was misidentified four times-twice as ethyl acetate (EA) and once each as MB and methyl 2-methyl butyrate (MMB). Without being limited to any particular theory, we propose that the completely incorrect assignment of BA is based on structural similarities, as twice it was misidentified as an ethyl ester and twice as a methyl ester of butyrate. These results are further illustrated in the PCA confusion matrix of FIG. 24, which shows the data for twenty-three different esters; the PCA confusion matrix of FIG. 25, which illustrates separately the confusion matrix data for esters EA, BA, MB, and MMB; and the PCA confusion matrix of FIG. 26, which illustrates separately the data for the esters LM and DM. These results indicate that the identification of the esters, LM, and DM (FIG. 26) is 100% accurate.

For mixture analysis, concentration runs of four esters, PA, ethyl valerate (EV), methyl nicotinate (MNI) and methyl 6-methyl nicotinate (MMNI) were performed with the nine esterases. The rates of the esterase reaction were plotted on a Lineweaver-Burk plot to determine the Km and Vmax and were used to identify subsequent mixtures of the four esters. For example, an equal volume mixture of PA/MMNI gave a reaction rate of $1\times10$ Ms$^{-1}$ for bacteria esterase 1, while the reaction rates of the individual components added to $1.3\times10$ Ms$^{-1}$. For all of the esterases, the esterase reaction of the mixture is a linear combination of the individual esters because the concentrations of the esters are well below the Km for the esterase.

In conclusion, the esterases' inherent cross-reactivity was incorporated into the array and the resulting nine-esterase array was able to distinguish over twenty individual analytes. The ability to distinguish such a diverse group of analytes using a limited suite of sensing materials demonstrates the utility of the approach. The microtiter plate format is an efficient and reproducible method for performing such analysis.

Example 2

Enzyme-Based Sensor Array

The present enzyme based sensor array is amenable to many different types of cross-reactive recognition elements, including cross-reactive recognition elements that are enzymes. To illustrate this point we used enzyme proteases to distinguish various protein substrates. Specifically, the present example demonstrates that different proteins can be distinguished by cross-reactive degradation using non-specific proteases. The sensor array consists of seven different proteases: proteinase K, chymotrypsin, papain, carboxypeptidase A, substilisin, protease (staphylococcus), and protease VII. Each protease has the capability of cleaving a particular peptide analyte to yield predictable and identifiable fragments, which are used to identify the peptide analyte. For example, reaction of chymotrypsin with a particular nine amino acid peptide analyte to yield three distinguishable primary amine products is shown below.

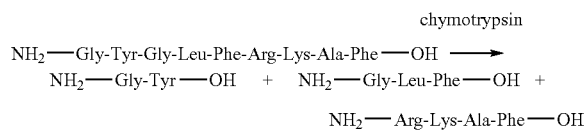

The resulting primary amines can be easily measured by any suitable amine reactive dye.

A typical reaction mixture consisted of for example, 1 μg of protein analyte and 0.5 units of protease. The reaction mixture was incubated with shaking at room temperature for one hour. Once the digestion was complete, 5 μl of o-phthaldialdehyde (OPA) dye solution was added, which reacts with all primary amines. The reaction of OPA with a primary amine is illustrated below.

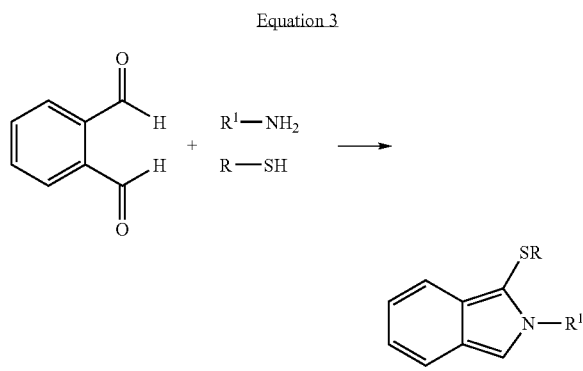

Reaction with OPA is allowed to proceed for two minutes before reading the plate. Those skilled in the art will readily appreciate that this reaction can easily be modified to suit different combinations of enzyme proteases and their substrates.

Those skilled in the art will further appreciate that any protein analyte can be used in a protease reaction. Exemplary protein analytes include catalase, fumarase, pepsin, glucose oxidase, cocarboxylase, alcohol oxidase, hemocyanin, β-lactoglobulin, tyrosinase, yeast enzyme concentrate, bovine albumin, galactose oxidase, lectin, peroxidase, lysozyme, acetylcholine esterase, aldehyde dehydrogenase, glutaminase, alcohol dehydrogenase, sheep albumin, human albumin, horse albumin, goat albumin, casein, alkaline phosphitase, urease, aconitase, hexokinase, avidin, cystatin, s-acetyl coenzyme A synthetase, papain, and IgG.

Figure 30:
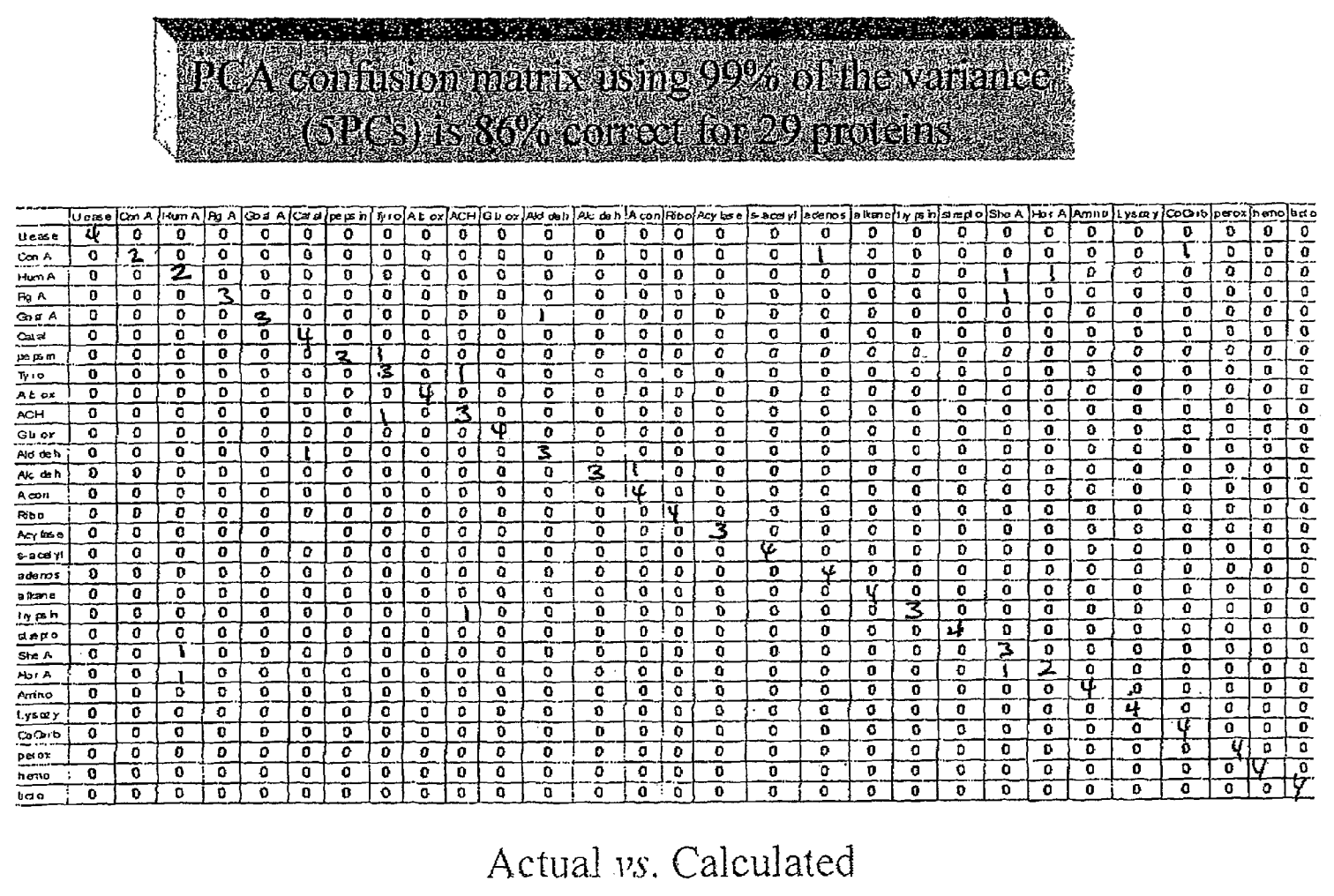

FIG. 30 depicts a PCA confusion matrix using 99% of the variance. Specifically, the calculated protein identity was compared with the actual identity of the protein to assess the accuracy of the assay. The results obtained were 86% correct for the 29 proteins tested. FIG. 31 shows a PCA confusion matrix for the various albumin protein analyte family members tested. The results in FIG. 31 reveal that 70% of the incorrect assignments were due to the albumins. This could be due to the similarity in structure and sequence of the albumin proteins.

Example 3

Immobilization of Cross-Reactive Recognition Elements

The present invention further provides an inventive sensor array system wherein the cross-reactive recognition element is immobilized onto a solid support made of different materials, such as polymer, silica, glass, metal and the like. For example, where the cross-reactive recognition element is an enzyme, the enzyme can be immobilized onto a solid support. In one embodiment, the cross-reactive recognition element is immobilized onto a bead. In general, one type of cross-reactive recognition element is immobilized on one bead. Other solid supports include columns, plates, vials, tubes, slides, pellets, disks, strips, wafers, electrical leads, electrodes, wires, fibers, gels, or particles such as cellulose beads, controlled pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, or glass particles coated with hydrophobic polymer, to name a few. Those skilled in the art will recognize that any of the cross-reactive recognition elements described herein may be immobilized onto a solid support using methods standard in the art.

According to the present invention, solid supports are synthesized to which the cross-reactive recognition element may be attached. In general, this may be accomplished by cross-linking the solid support to the cross-reactive recognition element of interest. For example, a bead may be attached to a cross-linker, which may then be cross-linked to a cross-reactive recognition element, e.g., an enzyme, for use in a sensor array. The beads in the sensor array may then be contacted with the analyte(s), as described herein above. Some examples of beads include microbeads (e.g., 3 μm, 5 μm, and 10 μm in diameter) and nanobeads (e.g., 100 nm, 90, nm and 10 nm in diameter), which may be made of silica, metal, or any standard polymer. The cross-linker may be incorporated into the bead at the time of bead synthesis, or alternatively, may be added to the bead after bead synthesis.

As but one example, amine reactive cross-linkers may be used to generate amine funtionalized beads. A cross-reactive recognition element, e.g., an enzyme, may be attached to the bead by cross-linking the amine on the bead to the amine on the cross-reactive recognition element. Some examples of amine reactive cross-linkers include disuccinimidyl suberate (DSS), disuccinimidyl tartrate (DST), dimethyl 3,3'-dithiobispropionate (DTBP), 3,3; dithiobis[sulfosuccinimidyl-2HCl]-propionate, disuccinimidyl glutarate (DSG), dithiobis [succinimidyl propionate] (DSP), dimethyl saberimidate.2HCl (DMS), dimethylpimelimadate.2HCl (DMP), dimethyl adipimidate.2HCl (DMA), 1,5 difluoro-2, 4-dinitrobenzene (DFDNB), bis [sulfosuccinimidyl] (Bs$^3$), bis[2-succinimidyloxycarbonyloxyethyl] sulfone (BSOCOES), and bis-[β-(4-azidosalicylamido) ethyl] disulfide (BASED), all of which are available from Pierce Chemical Company, Rockford, Ill.

As will be appreciated by those skilled in the art, the bead and the cross-reactive recognition element may be attached by cross-linkers other than amine reactive cross-linkers. For example, the bead and the cross-reactive recognition element may be attached by reaction of a carboxylic acid and an amine, a sulfhydryl and an amine, or an arginine and an amine. Such cross-linkers are also available from Pierce Chemical Company, Rockford, Ill.

The synthesis reaction involves contacting a cross-linker of choice, for example, an amine reactive cross-linker, with the solid support, e.g., beads, and an enzyme in a vial, which is shaken for 30 minutes. 1 µM glycine solution is then added to the vial to abate any reactive group and the beads are washed repeatedly. Those skilled in the art will further appreciate that the cross-reactive recognition element may be attached to the solid support simultaneously with the synthesis of the solid support.

Once synthesized, the beads containing the cross-reactive recognition elements are placed in complimentary wells of an etched optical imaging fiber from Illumina (San Diego, Calif.) (1 mm diameter with 3 or 5 µm wells). The fiber tip is then coated (e.g., spin coated) with a colorless polymer layer (e.g., acrylamide generated by the standard reaction of an amine reactive cross linker (bis(acrylamine)) with acrylamide) to secure the beads to their respective complimentary wells. The polymer layer further slows down the dissociation of $H^+$ into solution so that the dye can be used to measure the reaction.

Figure 27:
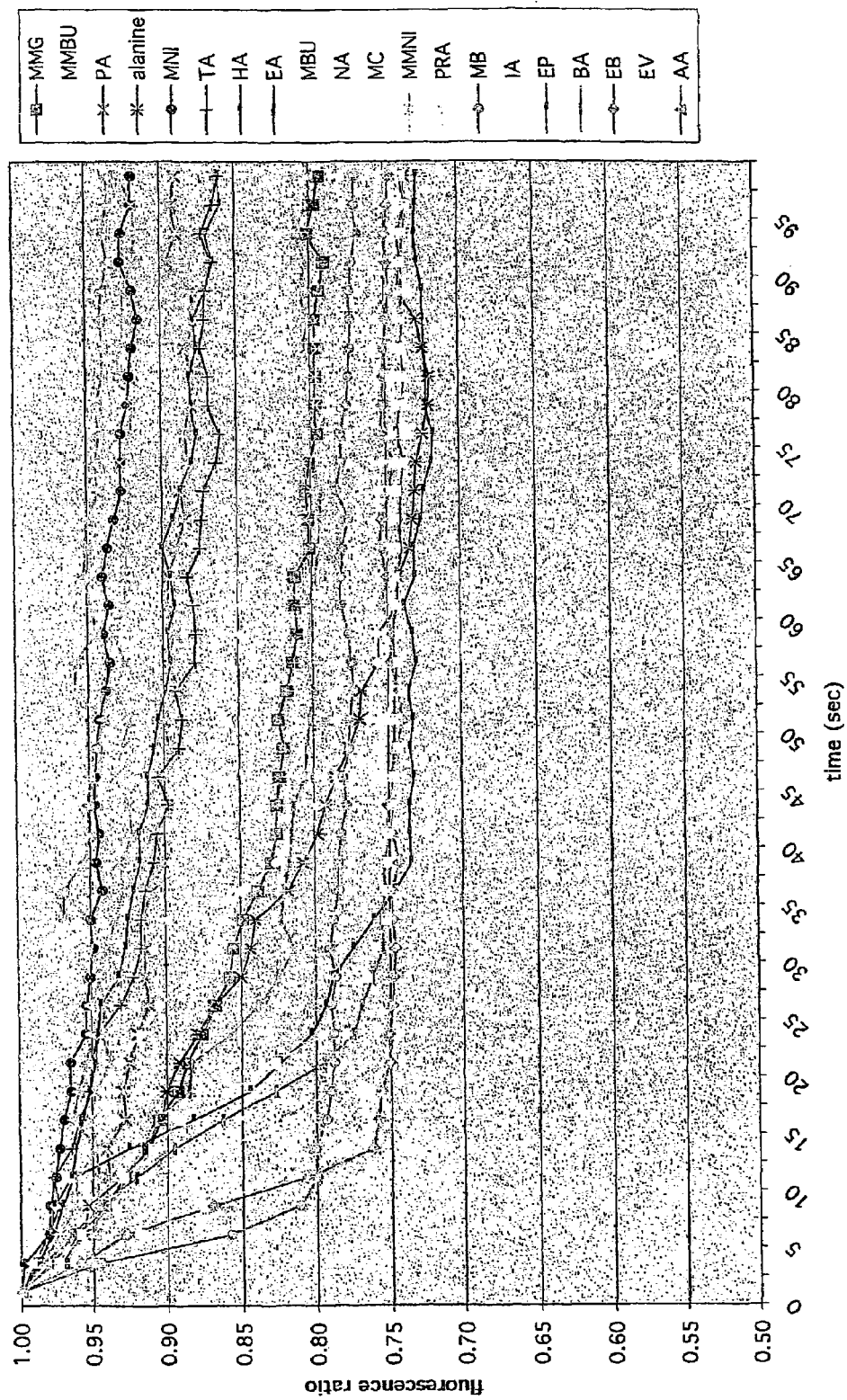
FIG. 27 depicts the fluorescence ratio versus time for rabbit esterase immobilized onto beads upon interaction with twenty different ester analytes.
Figure 28:
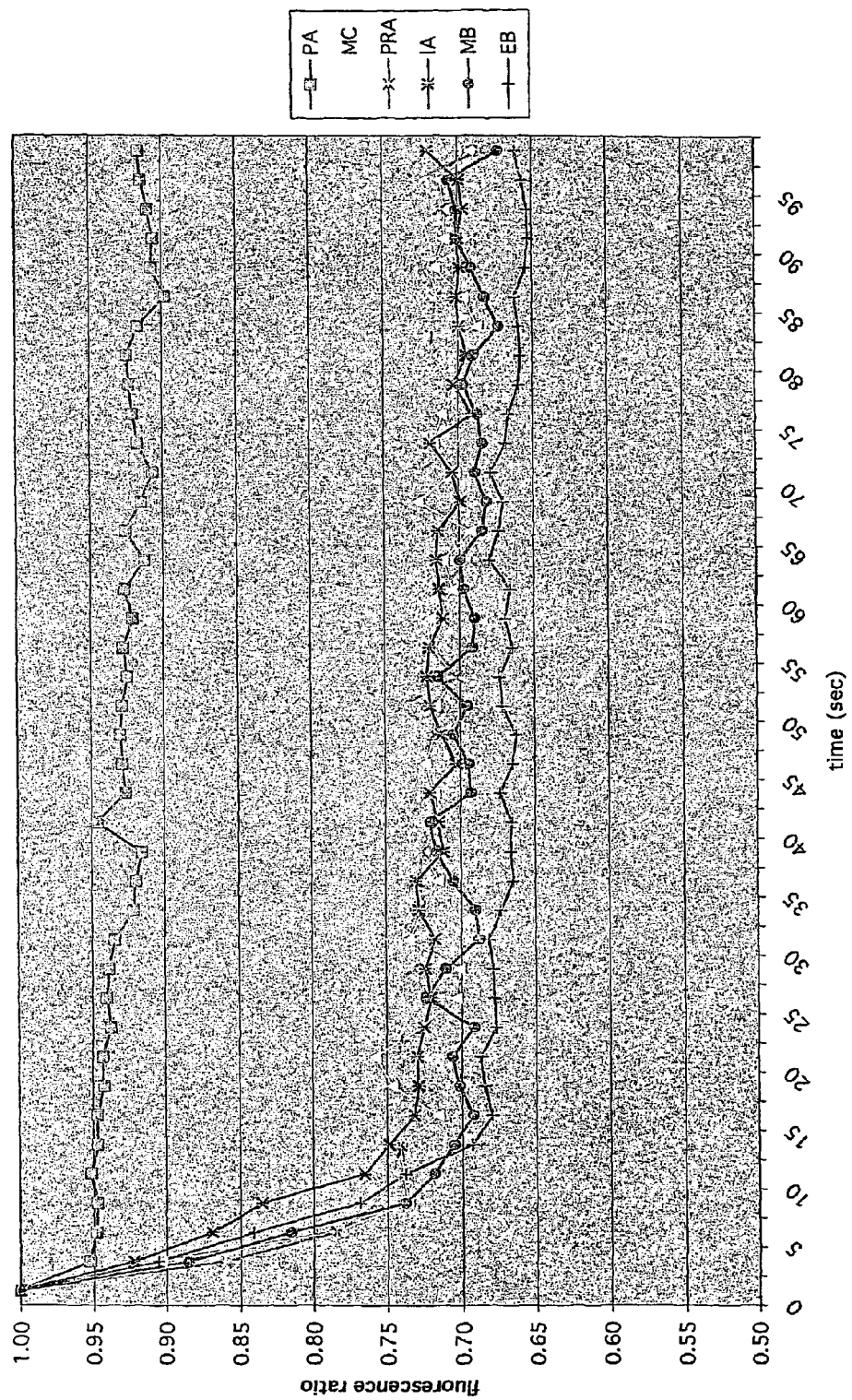
FIG. 28 depicts the fluorescence ratio versus time for bacteria esterase 1 immobilized onto beads with six different ester analytes.
Figure 29:
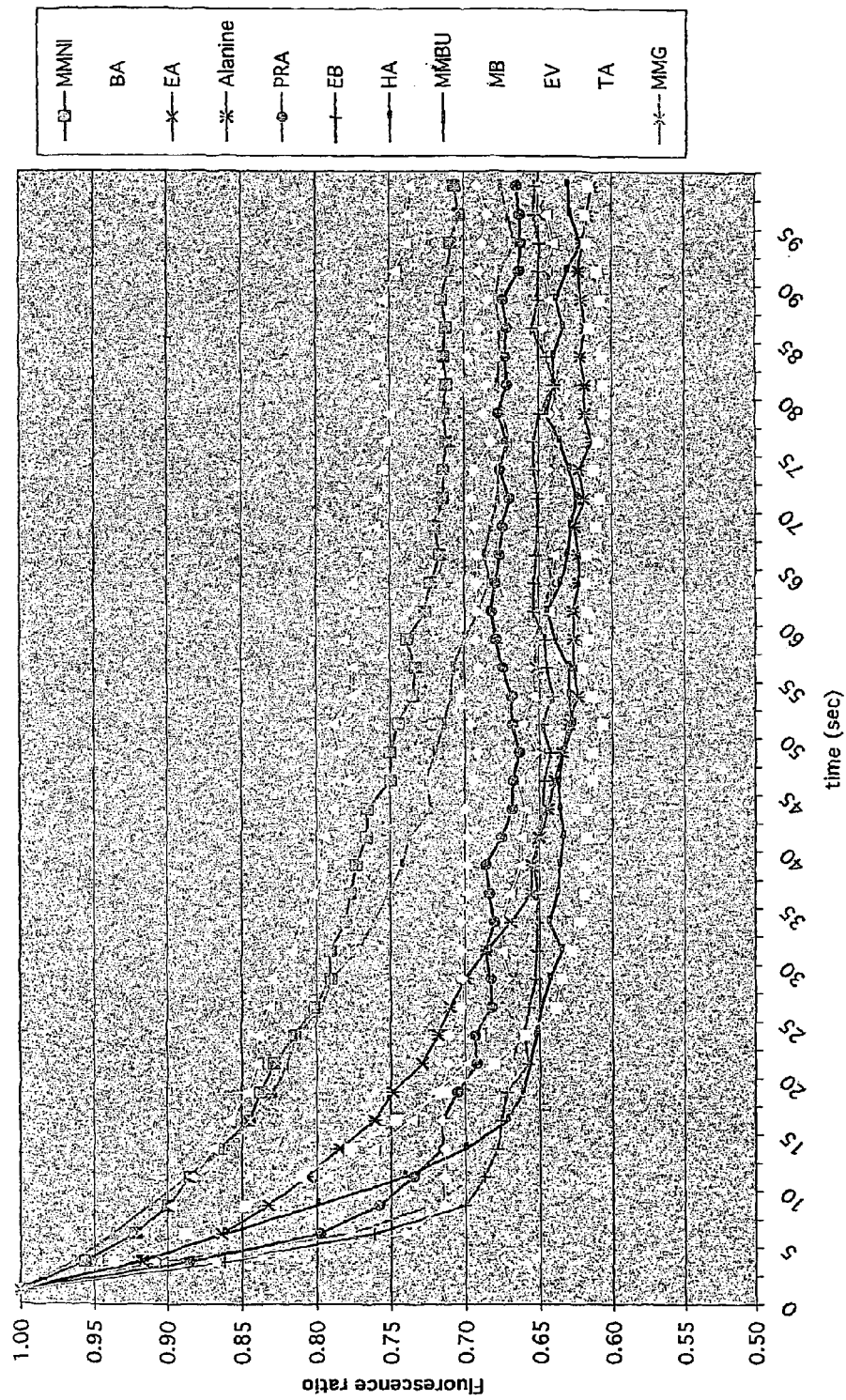
FIG. 29 depicts the fluorescence ratio versus time for porcine esterase immobilized onto beads with twelve different ester analytes.

FIGS. 27–29 illustrate reaction rates with each of twenty-three different esters obtained using beads having immobilized thereon one of three different esterases; rabbit esterase, bacteria esterase, and porcine esterase to demonstrate the success of this approach.

We claim:

1. A method for the analysis of analytes comprising steps of:
    contacting one or more analytes with a sensor system, wherein said sensor system comprises:
        one or more cross-reactive recognition elements, wherein each of said cross-reactive recognition elements is an enzyme or a protein receptor and wherein each of said cross-reactive recognition elements interacts directly with more than one species of liquid analyte of interest, whereby each of said cross-reactive recognition elements interacts in a different manner with each of said more than one species of liquid analyte of interest to produce a detectable event for each analyte of interest, wherein said detectable event is a detectable agent, a detectable change or both; and
    analyzing the detectable event produced for each analyte of interest to obtain information about said detectable event, process the information for data acquisition, and provide interpretation of data.

2. A method for the analysis of analytes comprising steps of:
    contacting one or more analytes with a sensor system, wherein said sensor system comprises:
        two or more cross-reactive recognition elements, wherein each of said cross-reactive recognition elements is an enzyme or a protein receptor and wherein each of said cross-reactive recognition elements interacts directly with more than one species of liquid analyte of interest, whereby each of said cross-reactive recognition elements interacts in a different manner with each of said more than one species of liquid analyte of interest to produce a detectable event for each analyte of interest, wherein said detectable event is a detectable agent, a detectable change or both; and
    analyzing the detectable event produced for each analyte of interest to obtain information about said detectable event, process the information for data acquisition, and provide interpretation of data.

3. A method for the analysis of analytes comprising steps of:
    contacting one or more analytes with a sensor system, wherein said sensor system comprises:
        two to five cross-reactive recognition elements, wherein each of said cross-reactive recognition elements is an enzyme or a protein receptor and wherein each of said cross-reactive recognition elements interacts directly with more than one species of liquid analyte of interest, whereby each of said cross-reactive recognition elements interacts in a different manner with each of said more than one species of liquid analyte of interest to produce a detectable event for each analyte of interest, wherein said detectable event is a detectable agent, a detectable change or both; and
    analyzing the detectable event produced for each analyte of interest to obtain information about said detectable event, process the information for data acquisition, and provide interpretation of data.

4. A method for the analysis of analytes comprising steps of:
    contacting one or more analytes with a sensor system, wherein said sensor system comprises:
        two to ten cross-reactive recognition elements, wherein each of said cross-reactive recognition elements is an enzyme or a protein receptor and wherein each of said cross-reactive recognition elements interacts directly with more than one species of liquid analyte of interest, whereby each of said cross-reactive recognition elements interacts in a different manner with each of said more than one species of liquid analyte of interest to produce a detectable event for each analyte of interest, wherein said detectable event is a detectable agent, a detectable change or both; and
    analyzing the detectable event produced for each analyte of interest to obtain information about said detectable event, process the information for data acquisition, and provide interpretation of data.

5. The method of any one of claims 1 to 4, wherein said sensor system includes a transducer.

6. The method of claim 5, wherein said transducer is selected from the group consisting of electrochemical transducer, optical transducer, thermal transducer, and acoustic transducer.

7. The method of claim 6, wherein said transducer is an optical transducer involving an energy transduction mode selected from the group consisting of absorbance, chemiluminescence, electrogenerated chemiluminescence, fluorescence, fluorescence lifetime, fiber optic waveguides, near-field microscopy, near-field spectroscopy, near-infrared, planar waveguides, surface enhanced raman, and surface plasmon resonance.

8. The method of claim 7, wherein said optical transducer comprises a pH sensitive dye.

9. The method of claim 8, wherein said pH sensitive dye is selected from the group consisting of fluorescein, carboxyfluorescein, SNAFL, SNARF, LysoSensor Green DND-189, Oregon Green NERF, LysoSensor Yellow/Blue DND-160, HPTS (pyranine), BCECF, BCPCF, and Bodipy.

10. The method of claim 7, wherein said optical transducer comprises an oxygen sensitive dye.

11. The method of claim 10, wherein said oxygen sensitive dye comprises $Ru(4,7\text{-diphenyl-1,10-phen})_3(Cl)_2$, or $Ru(bipy)_3Cl_2$.

12. The method of any one of claims 1 to 4, wherein the step of analyzing comprises utilizing a processing unit to provide interpretation of data.

13. The method of claim 12 further comprising processing interpreted data using chemoinformatics.

14. The method of claim 13, wherein said step of processing using chemoinformatics comprises interpreting data using computational analysis.

15. The method of any one of claims 1 to 4, wherein said cross-reactive recognition elements are provided in array format having a plurality of addresses, wherein each address in the array contains one cross-reactive recognition element.

16. The method of claim 15, wherein the array comprises a plurality of addresses, wherein two or more of the addresses contain the same type of cross-reactive recognition element.

17. The method of claim 15, wherein the array comprises a plurality of addresses, wherein each address contains the same cross-reactive recognition element.

18. The method of any one of claims 1 to 4, wherein said cross-reactive recognition elements are provided in array format having a plurality of addresses, wherein each address in the array contains more than one cross-reactive recognition element.

19. The method of any one of claims 1 to 4, wherein the cross-reactive recognition element is attached to a solid support.

20. The method of claim 19, wherein the solid support is a bead, or a resin.

21. The method of claim 20, wherein the solid support is a bead, each bead is attached to one type of cross-reactive recognition element, and wherein together the beads are provided in array format having a plurality of addresses, wherein each address in the array contains one bead.

22. The method of claim 21, wherein the array comprises a plurality of addresses, wherein two or more of the addresses contain beads having the same type of cross-reactive recognition element.

23. The method of claim 21, wherein the array comprises a plurality of addresses, wherein each address contains beads having the same cross-reactive recognition element.

24. The method of claim 20, wherein the solid support is a bead, each bead is attached to one type of cross-reactive recognition element, and wherein together the beads are provided in array format having a plurality of addresses, wherein each address in the array contains more than one bead.

25. The method of any one of claims 1 to 4, wherein each of said cross-reactive recognition elements is an enzyme selected from the group consisting of esterases, proteases, hydrolases, isomerases, lysases, transferases, oxido-reductases, and ligases.

26. The method of claim 25, wherein each of said cross-reactive recognition elements is an esterase selected from the group consisting of esterase from rabbit liver, esterase from porcine liver, acetylcholine esterase from electrophorous electricus, esterase from hog pancrease, esterase from hog liver, esterase from horse liver, esterase from *mucor miehei*, esterase from *bacillus* sp., and esterase from *bacillus thermoglucosidasius*.

27. The method of claim 25, wherein each of said cross-reactive recognition elements is a protease selected from the group consisting of proteinase K, chymotrypsin, papain, carboxypepsidase A, substilisin, protease (staphylococcus), and protease VII.

28. A method for the analysis of analytes comprising steps of:
    contacting one or more analytes with a sensor system, wherein said sensor system comprises:
        one or more cross-reactive recognition elements, wherein each of said cross-reactive recognition elements is an enzyme or protein receptor attached to a solid support and wherein each of said cross-reactive recognition elements interacts directly with more than one species of liquid analyte of interest, whereby each of said cross-reactive recognition elements interacts in a different manner with each of said more than one species of liquid analyte of interest to produce a detectable event for each analyte of interest, wherein said detectable event is a detectable agent, a detectable change or both; and
    analyzing the detectable event produced for each analyte of interest to obtain information about said detectable event, process the information for data acquisition, and provide interpretation of data.

29. The method of claim 28, wherein said sensor system includes a transducer.

30. The method of claim 29, wherein said transducer is selected from the group consisting of electrochemical transducer, optical transducer, thermal transducer, and acoustic transducer.

31. The method of claim 30, wherein said transducer is an optical transducer involving an energy transduction mode selected from the group consisting of absorbance, chemiluminescence, electrogenerated chemiluminescence, fluorescence, fluorescence lifetime, fiber optic waveguides, near-field microscopy, near-field spectroscopy, near-infrared, planar waveguides, surface enhanced raman, and surface plasmon resonance.

32. The method of claim 31, wherein said optical transducer comprises a pH sensitive dye.

33. The method of claim 32, wherein said pH sensitive dye is selected from the group consisting of fluorescein, carboxyfluorescein, SNAFL, SNARF, LysoSensor Green DND-189, Oregon Green, NERF, LysoSensor Yellow/Blue DND-160, HPTS (pyranine), BCECF, BCPCF, and Bodipy.

34. The method of claim 31, wherein said optical transducer comprises an oxygen sensitive dye.

35. The method of claim 34, wherein the oxygen sensitive dye comprises $Ru(4,7\text{-diphenyl-1,10-phen})_3(Cl)_2$, or $Ru(bipy)_3Cl_2$.

36. The method of claim 28 or 29, wherein the step of analyzing comprises utilizing a processing unit to provide interpretation of data.

37. The method of claim 36, further comprising processing interpreted data using chemoinformatics.

38. The method of claim 37, wherein said step of processing using chemoinformatics comprises interpreting data using computational analysis.

39. The method of claim 28 or 29, wherein the solid support is a bead, or resin.

40. The method of claim 39, wherein the solid support to which each of said cross-reactive recognition elements is attached is a bead and wherein together the beads are provided in array format having a plurality of addresses, whereby each address in the array contains one bead.

41. The method of claim 40, wherein the array comprises a plurality of addresses, wherein two or more of the addresses contain a bead containing the same type of cross-reactive recognition element.

42. The method of claim 40, wherein the array comprises a plurality of addresses, wherein each address contains a bead containing the same cross-reactive recognition element.

43. The method of claim 40, wherein the array comprises a plurality of addresses, wherein each address contains a bead containing a different cross-reactive recognition element.

44. The method of claim 40, wherein the array comprises a plurality of addresses, wherein two or more of the addresses contain a bead containing a different type of cross-reactive recognition element.

45. The method of claim 39, wherein the solid support to which each of said cross-reactive recognition elements is attached is a bead and wherein together the beads are provided in array format having a plurality of addresses, whereby each address in the array contains more than one bead.

46. The method of claim 28, wherein each of said cross-reactive recognition elements is an enzyme selected from the group consisting of esterases, proteases, hydrolases, isomerases, lysases, transferases, oxido-reductases, and ligases.

47. The method of claim 46, wherein each of said cross-reactive recognition elements is an esterase selected from the group consisting of esterase for rabbit liver, esterase from porcine liver, acetylcholine esterase from electrophorous electricus, cholesterol esterase from hog pancrease, esterase from hog liver, esterase from horse liver, esterase from *mucor miehei*, esterase from *bacillus* sp., and esterase from *bacillus* thermoglucosidasius.

48. The method of claim 46, wherein each of said cross-reactive recognition elements is a protease selected from the group consisting of proteinase K, chymotrypsin, papain, carboxypepsidase A, substilisin, protease (staphylococcus), and protease VII.

49. A method for the analysis of analytes in a liquid sample comprising steps of:
   providing a liquid sample comprising two or more analytes;
   providing a sensor system comprising two or more cross-reactive recognition elements, wherein:
      each of said cross-reactive recognition elements is an enzyme or a protein receptor;
      for each analyte, the sensor system includes at least first and second cross-reactive recognition elements, wherein at least one of first and second cross-reactive recognition elements interacts directly with said analyte in an analyte-recognition element interaction; and
      each analyte-recognition element interaction produces a detectable event, wherein said detectable event is a detectable agent, a detectable change or both;
   contacting the liquid sample with the sensor system so that interaction of any particular analyte with cross-reactive recognition elements generates a reproducible pattern of detectable events; and
   analyzing the pattern of detectable events to obtain information about said detectable events.

* * * * *